United States Patent [19]

Yabe et al.

[11] Patent Number: 5,487,376
[45] Date of Patent: Jan. 30, 1996

[54] WASHING APPARATUS FOR A PROTECTION COVER FOR AN ENDOSCOPE

[75] Inventors: Hisao Yabe; Yoshihiro Iida; Akira Suzuki; Hideo Ito; Yoshio Tashiro; Minoru Yamazaki; Osamu Tamada, all of Tokyo, Japan

[73] Assignee: Olympus Optical Co., Ltd., Tokyo, Japan

[21] Appl. No.: 37,405

[22] Filed: Mar. 26, 1993

[30] Foreign Application Priority Data

Feb. 25, 1993 [JP] Japan .................................. 5-007138 U
Mar. 1, 1993 [JP] Japan ...................................... 5-040014

[51] Int. Cl.⁶ ........................................................ A61B 1/00
[52] U.S. Cl. .......................... 600/121; 15/302; 134/168 C
[58] Field of Search ........................ 128/4, 6; 134/166 C, 134/168 C, 103.1, 102.1, 102.3; 15/302, 304

[56] References Cited

U.S. PATENT DOCUMENTS

| | | |
|---|---|---|
| 3,035,691 | 5/1962 | Rasmussen et al. . |
| 3,633,758 | 1/1972 | Morse . |
| 4,288,882 | 9/1981 | Takeuchi ..................................... 15/88 |
| 4,366,901 | 1/1983 | Short . |
| 4,646,722 | 3/1987 | Silverstein et al. . |
| 4,715,360 | 12/1987 | Akui et al. . |
| 4,721,097 | 1/1988 | D'Amelio . |
| 4,741,326 | 5/1988 | Sidall et al. . |
| 4,779,727 | 10/1988 | Taterka et al. . |
| 4,825,850 | 5/1989 | Opie et al. . |
| 4,858,001 | 8/1989 | Milbank et al. . |
| 4,869,238 | 9/1989 | Opie et al. . |
| 4,877,033 | 10/1989 | Seitz . |
| 4,878,485 | 11/1989 | Adair . |
| 4,947,827 | 8/1990 | Opie et al. . |
| 4,991,564 | 2/1991 | Takahashi et al. . |
| 4,991,565 | 2/1991 | Takahashi et al. . |
| 5,025,778 | 6/1991 | Silverstein et al. . |
| 5,042,112 | 1/1992 | Dunklee . |
| 5,050,585 | 2/1992 | Takahashi . |
| 5,105,942 | 4/1992 | van Veen et al. . |
| 5,131,537 | 7/1992 | Gonzales . |
| 5,198,894 | 3/1993 | Hicks . |
| 5,201,908 | 4/1993 | Jones . |
| 5,217,001 | 6/1993 | Nakao et al. . |
| 5,237,984 | 8/1993 | Williams, III et al. . |
| 5,301,657 | 4/1994 | Lafferty et al. . |

FOREIGN PATENT DOCUMENTS

| | | |
|---|---|---|
| 0341719A1 | 11/1989 | European Pat. Off. . |
| 0349479A1 | 1/1990 | European Pat. Off. . |
| 4325138 | 11/1992 | Japan . |

*Primary Examiner*—Richard J. Apley
*Assistant Examiner*—Beverly M. Flanagan
*Attorney, Agent, or Firm*—Stevens, Davis, Miller & Mosher

[57] ABSTRACT

In an endoscope system including an endoscope having an insertion section insertable into a cavity under inspection and an operation section to which a proximal end of the insertion section is connected, and a disposable protection cover having an insertion section cover for covering the insertion section of the endoscope and an operation section cover for covering said operation section of the endoscope, said operation section cover is constructed such that it can be commonly used to cover operation sections of a plurality of endoscopes. Upon removing the insertion section of the endoscope from the insertion section cover, the insertion section section cover is supported by a supporting apparatus including a proximal end supporting unit for supporting a proximal end of the insertion section cover and a distal end supporting unit for supporting a distal end of the insertion section cover. The contaminated insertion section cover can be supported by the supporting apparatus such that the insertion section cover is brought into contact with a floor on an examination room.

3 Claims, 23 Drawing Sheets

FIG_1
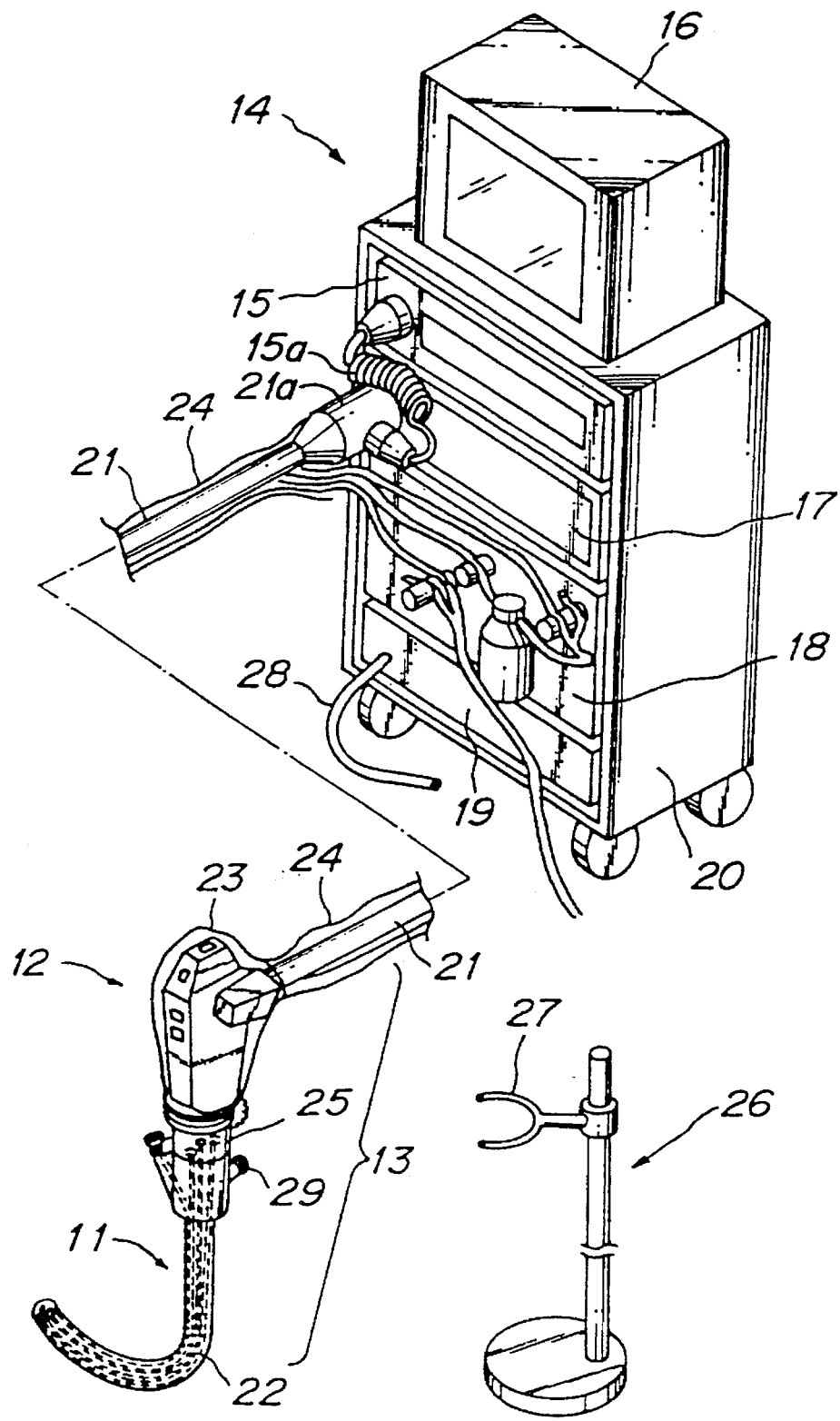

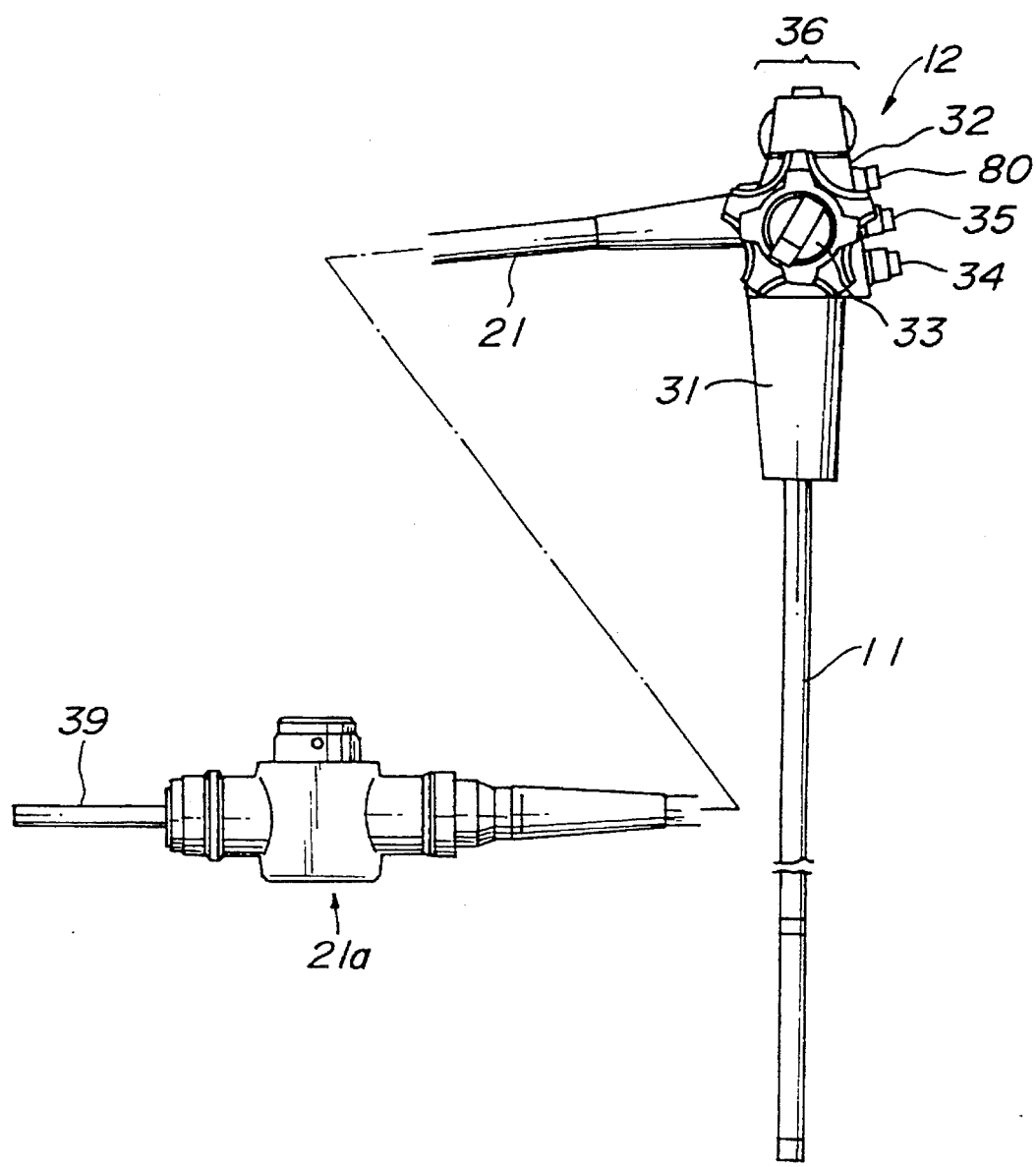
FIG_2

FIG_3
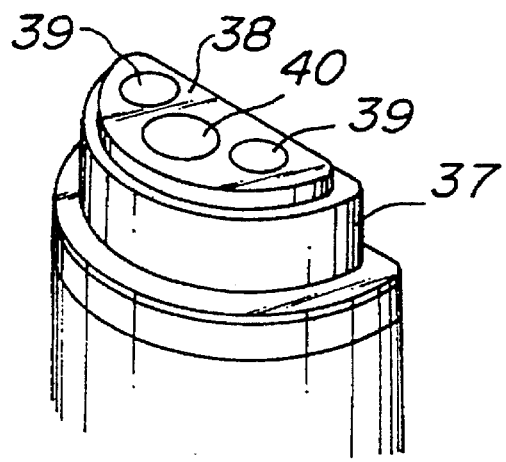
FIG_4
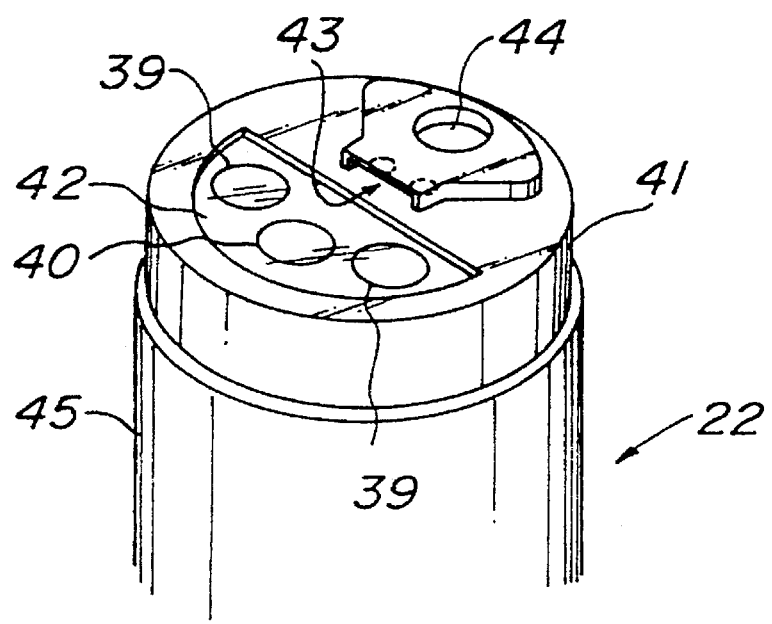

FIG_6
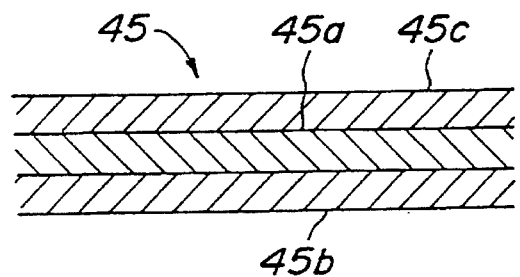
FIG_7
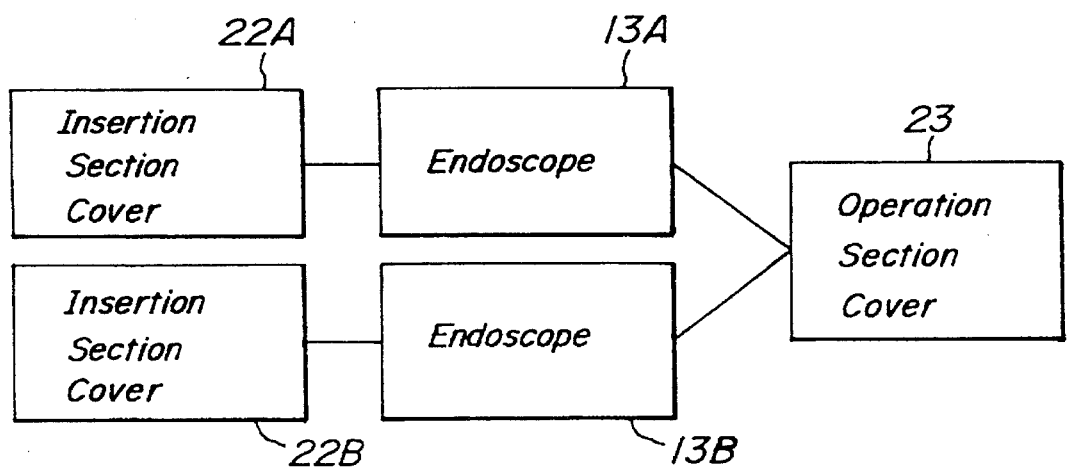

FIG_8
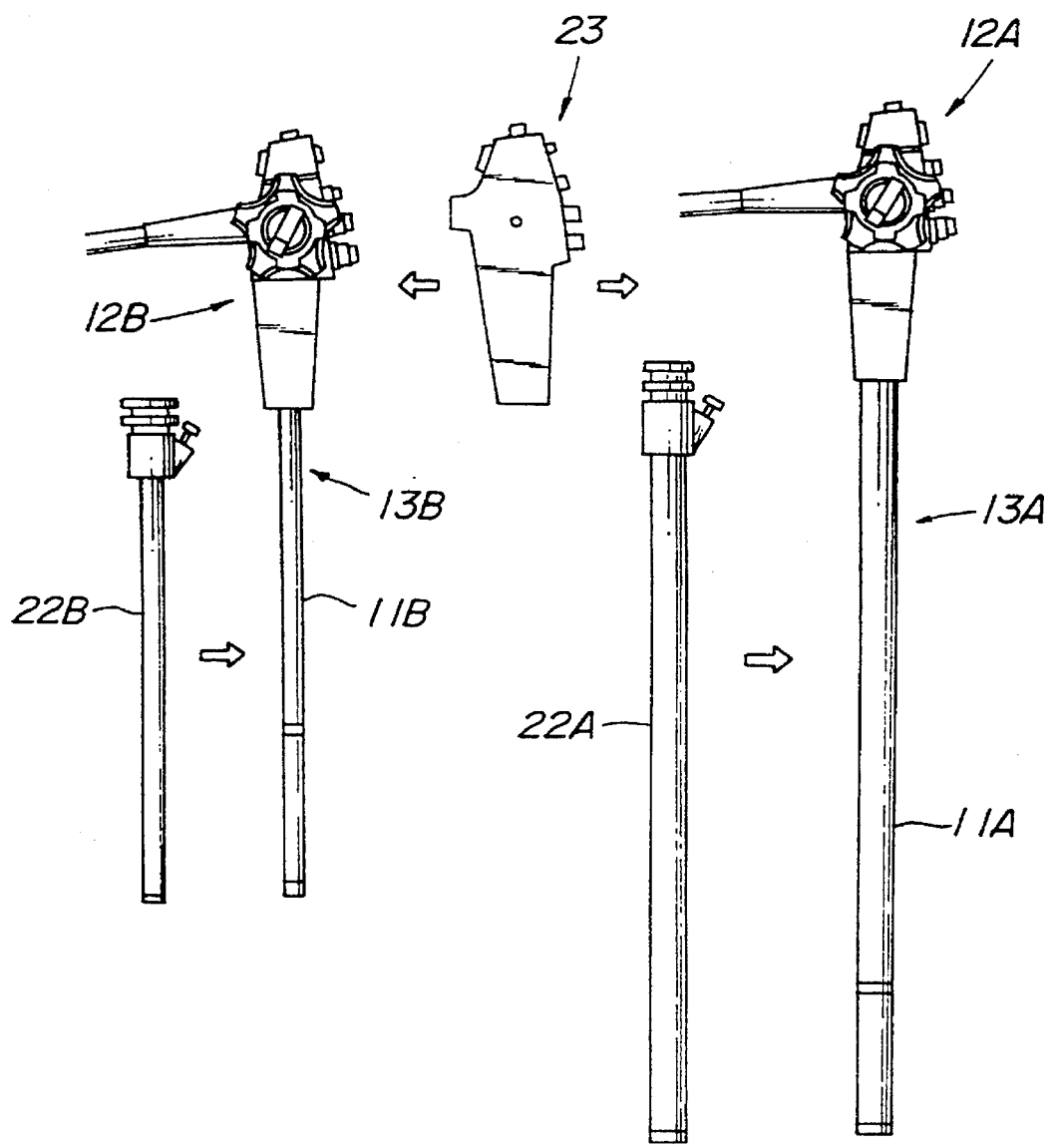

FIG_9
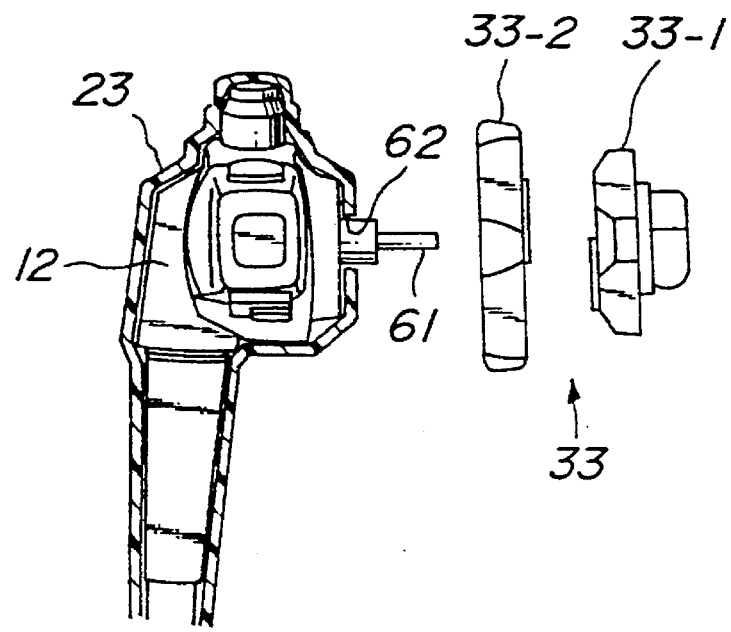
FIG_10
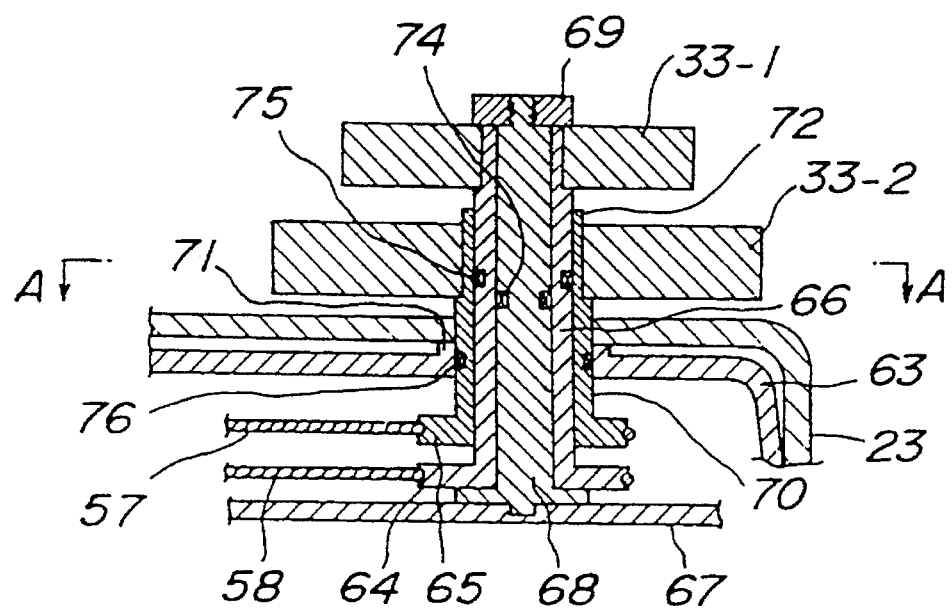

FIG_11
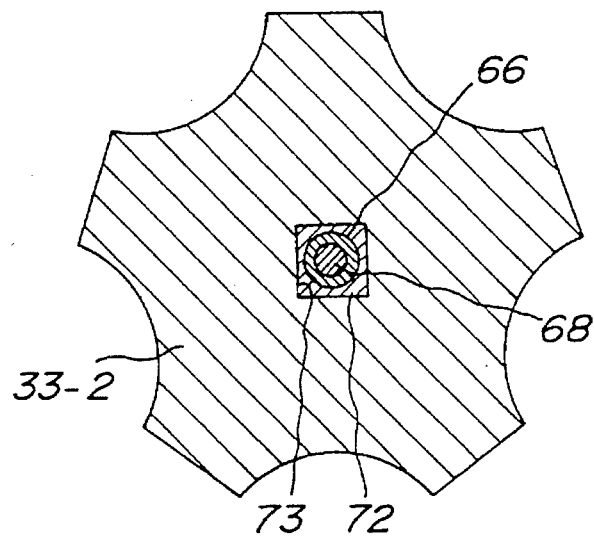
FIG_12
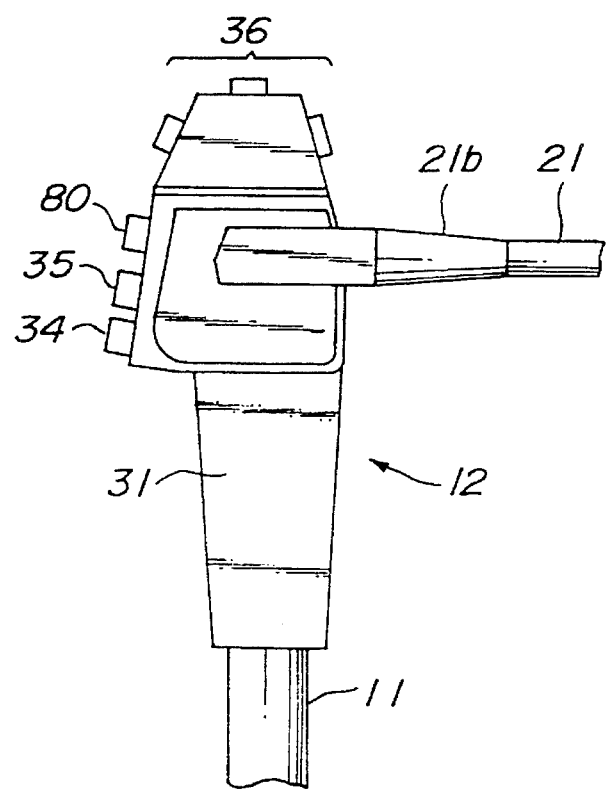

FIG_13
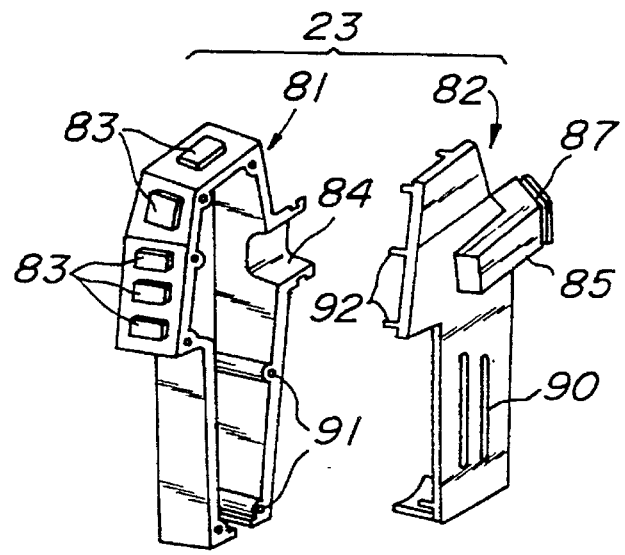
FIG_14
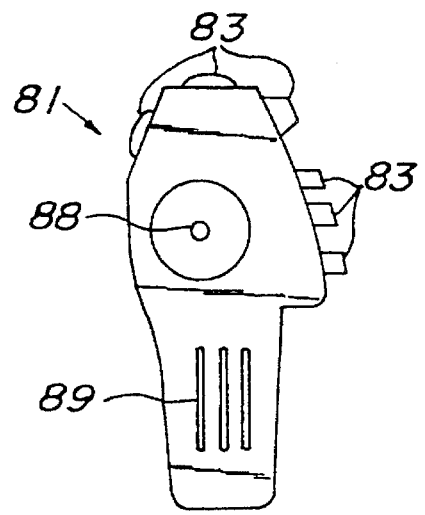

FIG_15
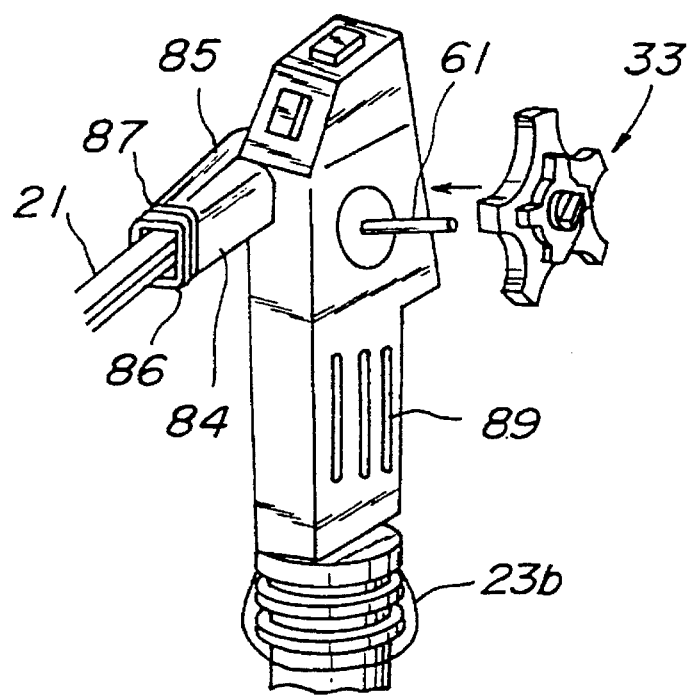
FIG_16
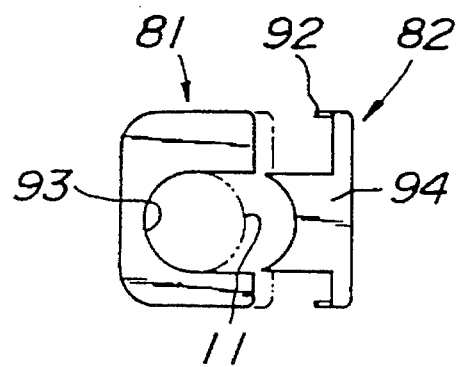

FIG_17A
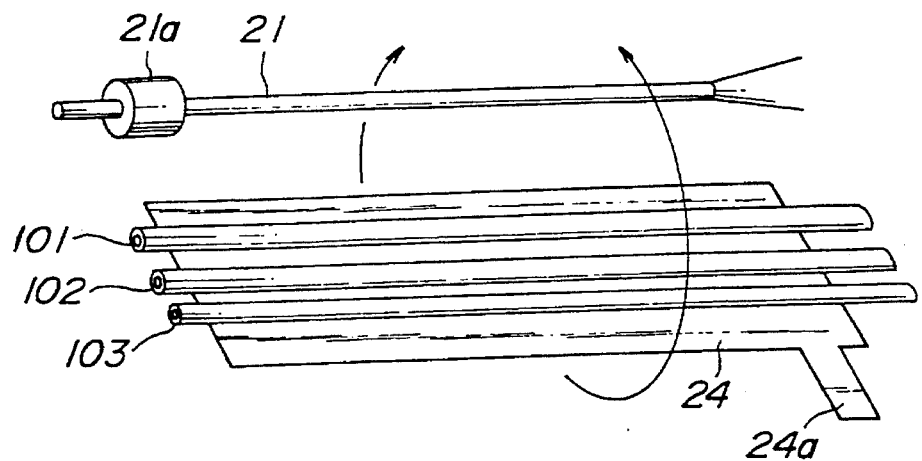
FIG_17B
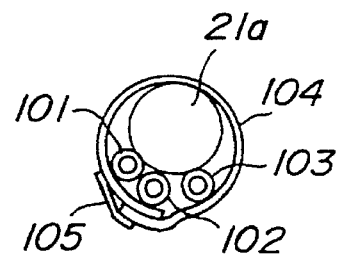
FIG_18
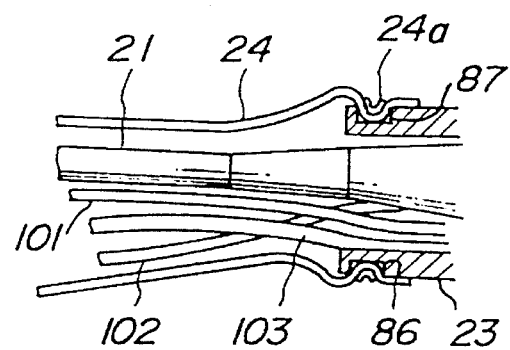

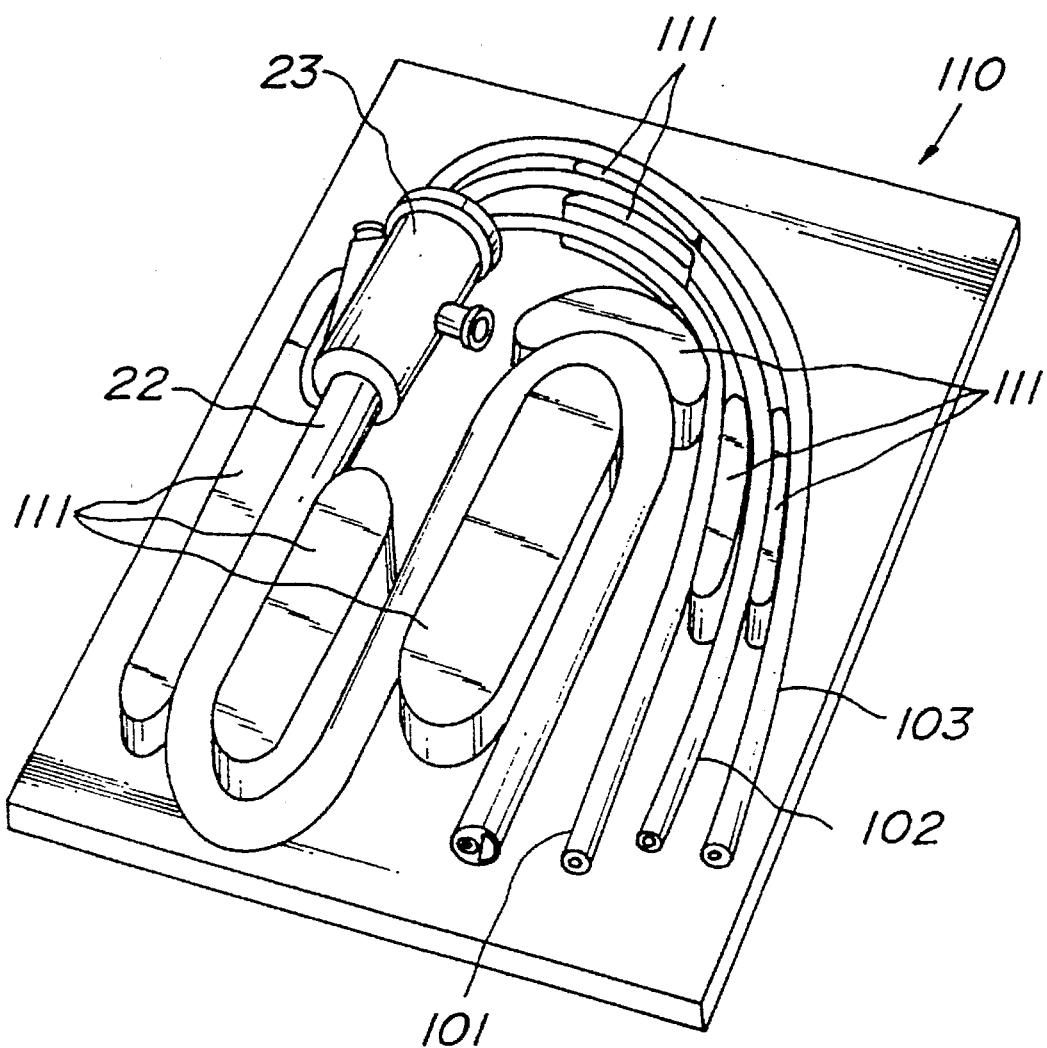
FIG_19

FIG_20
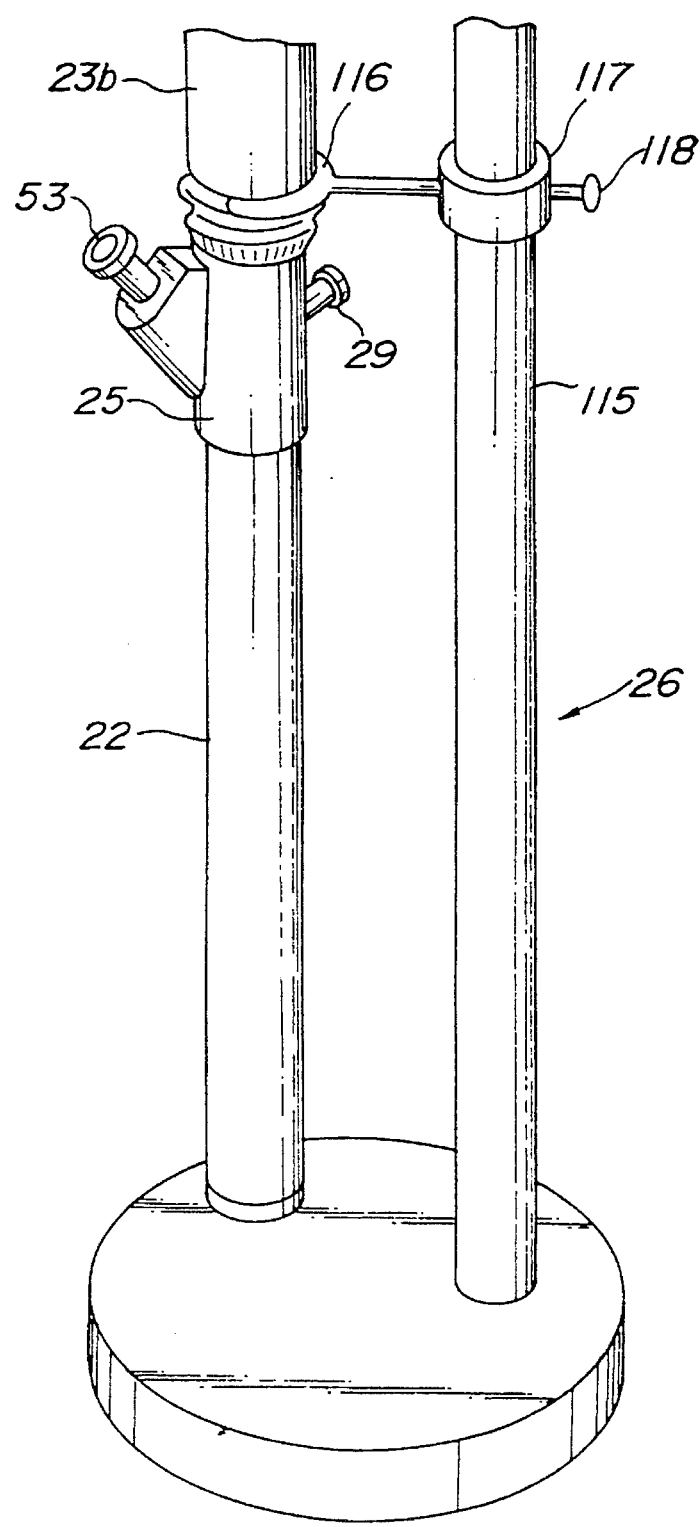

FIG_21
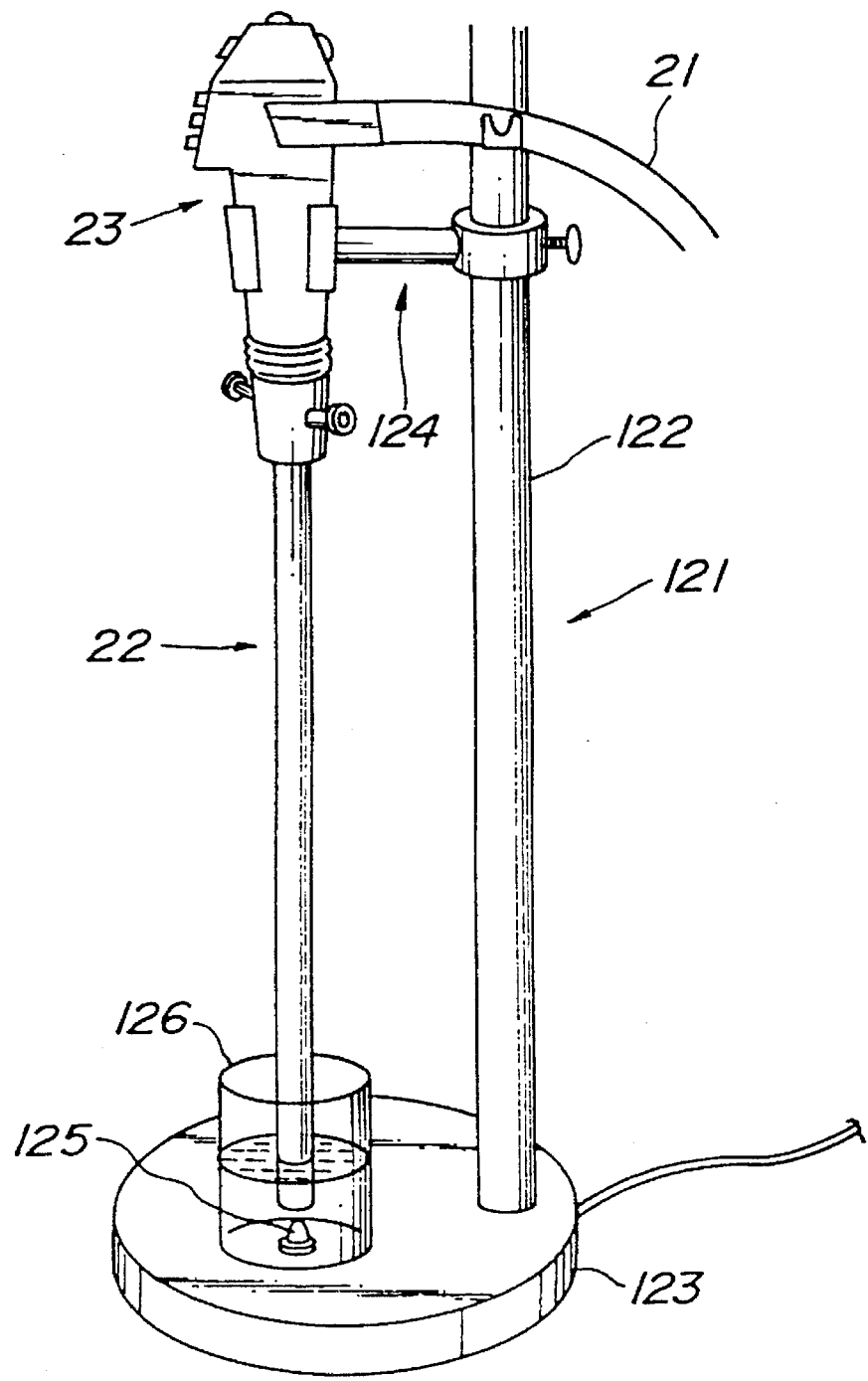

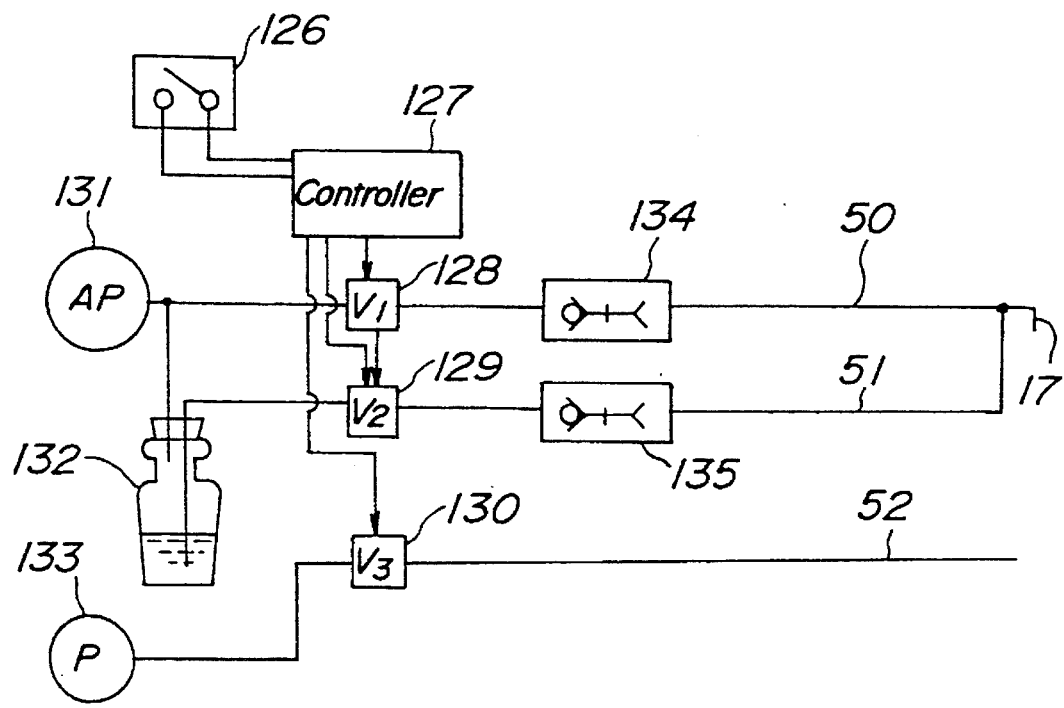

FIG_24
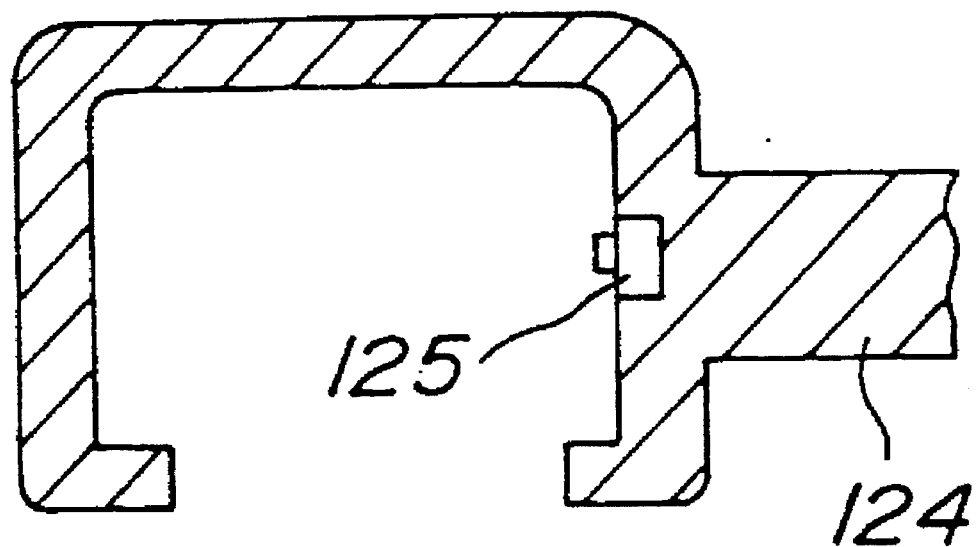

FIG_27A
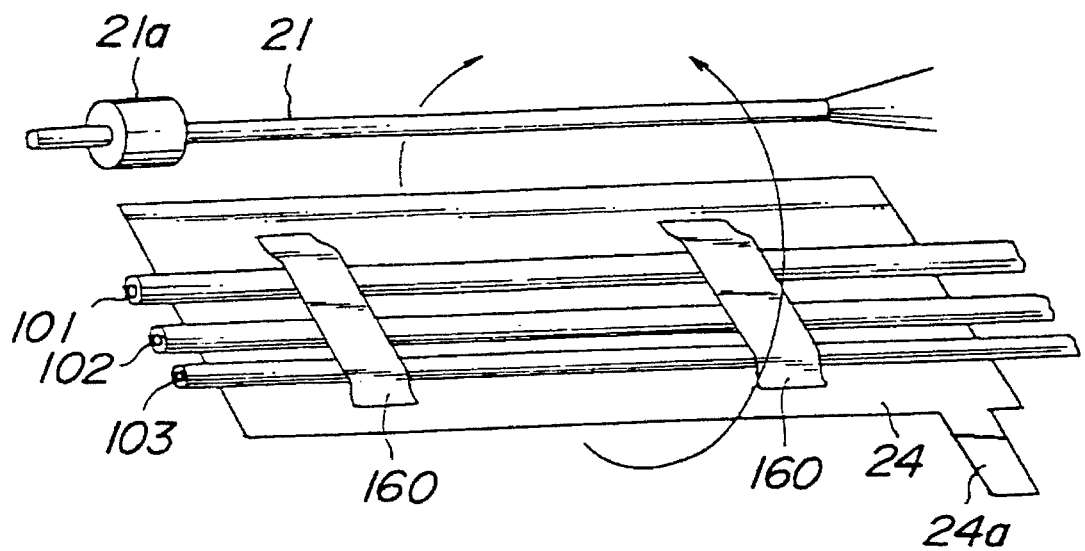
FIG_27B
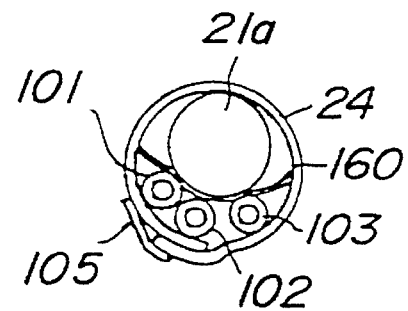

FIG_28
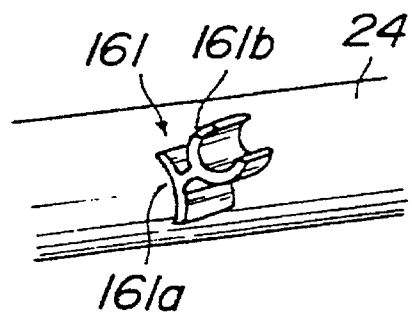
FIG_29
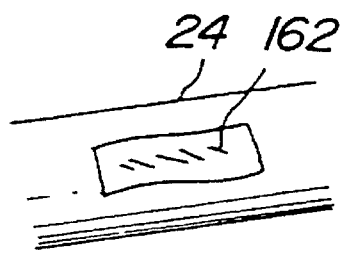
FIG_30
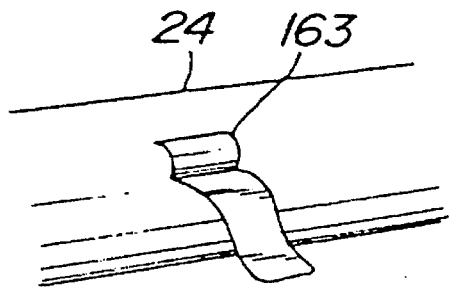

FIG_32

WASHING APPARATUS FOR A PROTECTION COVER FOR AN ENDOSCOPE

BACKGROUND OF THE INVENTION

1. Field of the Invention

The present invention relates to an endoscope system including an endoscope having an insertion section to be insertable into a cavity under inspection and an operation section to which a proximal end of the insertion section is connected, and a disposable protection cover having an insertion section cover for covering the insertion section of the endoscope and an operation section cover for covering the operation section of the endoscope.

2. Related Art Statements

An endoscope system has been widely utilized for providing diagnostic and therapeutic indications for coeliac cavities of patients and for internal inspection of mechanical structures. To this end, various kinds of endoscopes have been developed. For instance, in order to inspect or treating the oesophagus, stomach and duodenum, upper endoscopes have been utilized. Further, colonoscopes have been developed to examine colons and sigmoidoscopes have been proposed to inspect rectums and sigmoid colons. When the endoscope, is used an insertion portion of the endoscope has to be inserted into a cavity of a patient, so that the outer surface of the insertion section of the endoscope is contaminated with living tissues and liquids. Such a contaminated endoscope could not be successively used for other patients. Therefore, once the endoscope is used to diagnose and/or treat a patient, it is necessary to clean and sterilize the endoscope. Of course, the cleaning of the endoscope requires a substantial amount of time and during this cleaning time, it is impossible to perform the endoscopic procedure by using this endoscope. In order to mitigate such an idle time, it is necessary to prepare a large number of endoscopes. However, endoscopes are rather expensive, so that it is practically difficult to prepare a large number of endoscopes, particularly in a small hospital or clinic. Therefore, in almost all hospitals and clinics, in practice, after the endoscope has been used for examining or treating a patient, the endoscope is immediately cleaned. Typically, this cleaning requires several minutes to ten minutes. In order to effect complete washing and sterilization, the cleaning has be to performed for several tens of minutes.

Further, the endoscope has various channels such as an air channel, a water channel, a suction channel, and a forceps channel which extend along the insertion section from a proximal end to a distal end thereof, and these channels, except the forceps channel, are connected via tubes to respective devices such as an air supply pump, a water supply pump, a water suction pump and an air suction pump. These channels are subjected to the contact with living tissues and liquids. However, in order to clean these channels of the endoscope completely, a relatively long period of time is required. Thus, the endoscope can not be utilized efficiently during the long cleaning time. In a large hospital or clinics, a large number of endoscopes may be prepared in order to mitigate the problem of cleaning time. However, this solution results in an increase in the operating costs. Further, in small clinics, it is practically impossible to prepare a number of expensive endoscopes.

Moreover, the endoscope might be broken during cleaning and the usable life of the endoscope is liable to be shortened by the cleaning.

In order to avoid the above explained various problems, there has been proposed an endoscope system, in which the endoscope is covered with a disposable protection sheath-like cover having channels formed therein. For instance, U.S. Pat. Nos. 4,721,097, 4,741,326, 4,825,850, 4,869,238, 4,991,564, 4,991,565, 5,050,585 disclose various kinds of disposable protection sheath-like covers having channels formed therein. In U.S. Pat. No. 4,646,722, there is shown an endoscope system in which the endoscope is covered with a protection sheath, while a tube having channels formed therein is inserted into a U-shaped cutout formed in an outer surface of the endoscope along a longitudinal axis thereof. Upon diagnosis, the insertion section of the endoscope is covered with the protection sheath, and after the inspection, the sheath is removed from the insertion section and is then discarded. Therefore, it is no longer necessary to clean the endoscope after every the inspection.

In the above mentioned U.S. Patent Specifications, the protection sheath-like cover is constructed to cover only the insertion section of the endoscope, but does not cover an operation section of the endoscope. It should be noted that the operation section of the endoscope is handled by doctors and operators and thus is brought into contact with the living tissues and liquids of a patient. Therefore, in order to remove the contamination of the operation section of the endoscope due to such living tissues and liquids, it is advantageous to cover not only the insertion section, but also the operation section of the endoscope. In European Patent Publication No. 0 349 479 A1, there is disclosed an endoscope system, in which not only the insertion section, but also the operation section of the endoscope are covered with a disposable protection cover. That is to say, the protection cover comprises a sheath-like portion for covering the insertion section of the endoscope and a bag-like portion for covering the operation section, said sheath-like portion and bag-like portion being integrally formed. It has been also proposed to form the sheath-like portion and bag-like portion as separate covers. For instance, in European Patent Publication No. 0 341 719 A1, there is proposed another known endoscope system, in which an insertion section of an endoscope is covered with a sheath-like disposable protection cover and an operation section of the endoscope is covered with a bag-like cover disposable protection which is mated or joined with the sheath-like cover in order to prevent the contamination through the junction of the sheath-like cover and the bag-like cover.

At the actual examination site, various kinds of endoscopes having different lengths, shapes and dimensions are prepared. Particularly, the shape and dimensions of the operation sections differ from respective endoscopes. In such a case, it is necessary to prepare a plurality of operation section covers having different shapes and dimensions, and therefore the operator has to select a desired operation section cover from a plurality of operation section covers. This selection is rather cumbersome and there is the danger that the suitable operation section cover sill not be selected. If an incompatible operation section cover for the endoscope to be used is erroneously selected, the operation section might not be covered sufficiently or the operation section cover might be broken.

Further, after the examination, the endoscope has to be removed from the disposable protection cover and the used cover has to be discarded. In order to carry out this removing operation in an easy and positive manner, it is necessary to use a supporting apparatus which can support the endoscope with the disposable protection cover. When a part of the used disposable protection cover is brought into contact with the floor of the examination room during the removing operation, the floor is contaminated by the used disposable protection cover. However, there has not been proposed such a supporting apparatus.

SUMMARY OF THE INVENTION

The present invention has for its object to provide a novel and useful endoscope system in which the above explained erroneous selection of the operation section cover can be positively prevented and thus the examination procedure can be performed easily and reliably.

An embodiment of the invention provides a novel and useful apparatus for supporting the used assembly of the endoscope and disposable protection cover, in which the operation for removing the endoscope from the protection cover can be carried out easily and efficiently without causing the contamination of the floor or other things in the examination room due to the contact with the used assembly.

It is still another object of the invention to provide a novel and useful apparatus for washing a used disposable protection cover after the examination in an easy and efficient manner.

According to a first aspect of the invention, in an endoscope system including a plurality of endoscope systems, each having an insertion section insertable into a cavity under inspection and an operation section to which a proximal end of the insertion section is connected, and a plurality of disposable protection covers, each having an insertion section cover and an operation section cover for covering an insertion section and an operation section, respectively of an endoscope, the improvement being characterized in that each of said disposable protection covers is constructed such that said operation section cover can be used commonly for covering the operation sections of said plurality of endoscopes.

According to a second aspect of the invention, in an endoscope system including an endoscope having an insertion section insertable into a cavity under inspection and an operation section to which a proximal end of the insertion section is connected and a disposable protection cover having an insertion section cover and an operation section cover for covering an insertion section and an operation section, respectively of an endoscope, the improvement being characterized in that the endoscope system comprises an apparatus for supporting an assembly of the endoscope and disposable protection cover at at least two points.

In a preferable embodiment of the endoscope system according to the invention, the supporting apparatus comprises a proximal end supporting unit for supporting a proximal end of the insertion section cover, a distal end supporting unit for supporting a distal end of the insertion section cover and a stand on which said proximal and distal end supporting units are provided. By adjusting a distance between said proximal and distal end supporting units along the stand in accordance with a length of the insertion section cover, the insertion section cover can be effectively prevented from being brought into contact with the floor in the examination room.

According to a third aspect of the invention, an apparatus for washing a disposable protection cover for use in an endoscope system including an endoscope having an insertion section insertable into a cavity under inspection and an operation section to which a proximal end of the insertion section is connected and a disposable protection cover having an insertion section cover for covering the insertion section of the endoscope and an operation section cover for covering the operation section of the endoscope, the insertion section cover having air supply conduit channel, water supply conduit channel and suction channel formed therein, comprises:

means for supporting the disposable protection cover in such a posture that the distal end of the insertion section cover is directed downward;

means for containing a liquid into which the distal end of the insertion section cover is immersed; and means for automatically starting a washing operation, the washing operation being performed by supplying air through the air supply conduit channel, supplying water through the water supply conduit channel and sucking liquid through the suction channel successively in this order.

In a preferable embodiment of the washing apparatus according to the invention, the means for automatically starting the washing operation comprises a switch for detecting a condition that the liquid containing means is set in the washing apparatus. It should be noted that the means for automatically starting the washing operation comprises a switch provided in the supporting means for detecting a condition that the disposable protection cover is set on the supporting means.

BRIEF DESCRIPTION OF THE DRAWINGS

FIG. 1 is a perspective view showing the whole construction of an embodiment of the endoscope system according to the invention;

FIG. 2 is a front view illustrating the construction of the operation section of the endoscope shown in FIG. 1;

FIG. 3 is a perspective view depicting the distal end of the insertion section of the endoscope;

FIG. 4 is a perspective view illustrating the construction of the distal end of the insertion section cover;

FIG. 6 is a cross sectional view depicting the construction of the flexible cover tube of the insertion section cover according to the invention;

FIG. 7 is a schematic diagram representing the general construction of the endoscope system according to the invention;

FIG. 8 is a side view cut showing the different endoscopes for which the operation section cover can be commonly used;

FIG. 9 is a cross sectional view showing the angle knobs detached from the shaft of the operation section;

FIG. 10 is a cross sectional view depicting the detailed construction of the shaft;

FIG. 11 is a cross sectional view cut along a line 11—11 in FIG. 10;

FIG. 12 is a side view showing another embodiment of the operation section of the endoscope;

FIG. 13 is a perspective view illustrating an embodiment of the operation section cover according to the invention;

FIG. 14 is a side view depicting the main body of the insertion section cover shown in FIG. 13;

FIG. 15 is a perspective view showing the insertion section cover of FIG. 13;

FIG. 16 is a bottom view illustrating the insertion section cover of FIG. 13;

FIGS. 17A and 17b are a perspective view and an end view, respectively showing an embodiment of the universal cord cover according to the invention;

FIG. 18 is a cross sectional view depicting the universal cord covered with the universal cord cover;

FIG. 19 is a perspective view showing an embodiment of the cover package;

FIG. 20 is a perspective view illustrating an embodiment of the cover supporting device according to the invention;

FIG. 21 is a perspective view showing an embodiment of the apparatus for washing the used cover according to the invention;

FIG. 22 is a diagram representing the construction of the washing apparatus;

FIG. 23 is a timing chart for explaining the operation of the washing apparatus;

FIG. 24 is a cross sectional view showing another embodiment of the switch for automatically starting the washing operation;

FIGS. 27A and 27B are a perspective view and an end view, respectively depicting another embodiment of the universal cord cover according to the invention;

FIG. 28 is a perspective view showing an embodiment of the tube fixing member according to the invention;

FIG. 29 is a perspective view representing another embodiment of the tube fixing member according to the invention;

FIG. 30 is a perspective view illustrating another embodiment of the tube fixing member according to the invention;

EXPLANATION OF THE PREFERRED EMBODIMENTS

Figure 5:
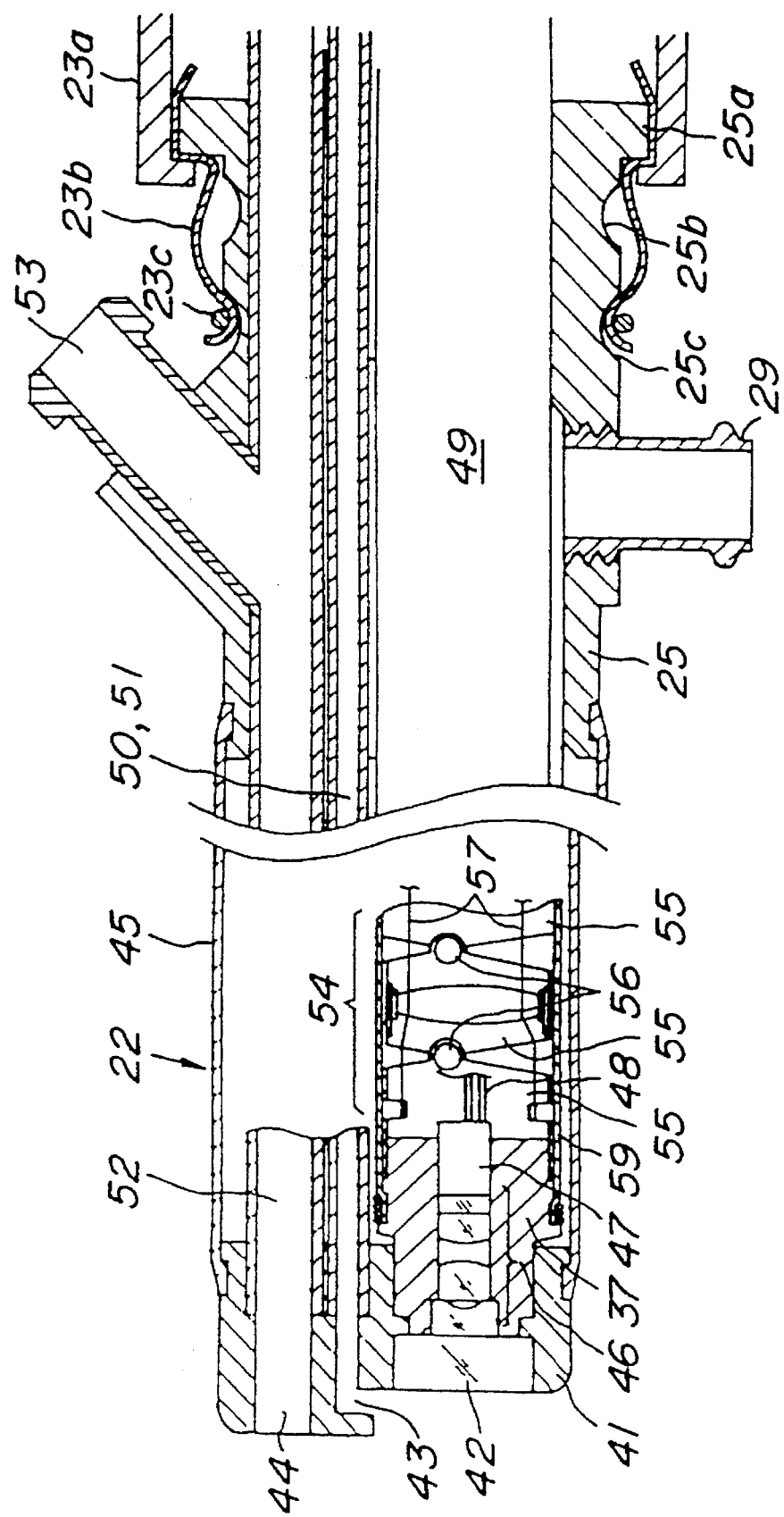
FIG. 5 is a longitudinal cross sectional view showing the endoscope system shown in FIG. 1.

FIG. 1 is a schematic view showing an embodiment of the endoscope system according to the invention including an endoscope apparatus and disposable protection cover. The endoscope apparatus comprises an endoscope 13 having an insertion section 11 and an operation section 12 with which a proximal end of the insertion section is coupled, and an external apparatus 14 coupled with the endoscope 13. The external apparatus 14 comprises a video processor 15 having a circuit for driving a solid state image sensor provided within a distal end of the insertion section 11 and a circuit for processing an image signal read out of the solid state image sensor, a monitor device 16 for displaying an image of an object under inspection by processing the image signal supplied from the video processor 15, a light source device 17 for emitting light for illuminating an inside of a cavity by means of a light guide optical fiber bundle extending within the insertion section 11, a fluid control device 18 for supplying air and water and sucking liquids, and an inflator 19 for inflating the disposable protection cover in order to inflate the disposable protection cover such that the insertion section 11 of the endoscope 13 can be easily inserted into and removed from the disposable protection cover as will be explained later in detail. These devices are installed in a box 20 having casters. The video processor 15 and light source device 17 are coupled with the operation section 12 of the endoscope 13 by means of signal conductors and light guide optical fiber bundle provided in a universal cord 21, and the fluid control device 18 is coupled with conduit channels provided within the disposable protection cover by means of conduit tubes arranged along the universal cord 21. The construction and operation of the above mentioned devices except for the inflator 19 are well known in the art, so that the detailed explanation thereof is dispensed with.

The disposable protection cover of the present embodiment comprises an insertion section cover 22 for covering the insertion section 11 of the endoscope 13, an operation section cover 23 for covering the operation section 12 of the endoscope and a universal cord cover 24 for covering the universal cord 21. These disposable protection covers 22, 23 and 24 are formed separately from each other, and suitable coupling mechanisms are provided between junctions thereof in order to avoid a possible contamination through the junctions.

The protection covers 22, 23 and 24 may be made of various materials. For instance, flexible vinyl and rubber may be used as a soft material and rigid or semi-rigid plastics may be used as a hard material. It should be noted that the protection covers 22, 23 and 24 are not always necessary to be made of the same material, but may be made of different materials. For instance, the insertion section cover 22 may be made of flexible rubber, the operation section cover 23 may be made of rigid plastics and the universal cord cover 24 may be made of semi-rigid vinyl.

Prior to the actual examination, a set of protection covers is removed from a package and a connecting portion 25 made of rigid or semi-rigid plastics and provide at a proximal end of the insertion section cover 22 is hung from a cover supporting member 27 of a cover supporting device 26. In order to prevent the connecting portion 25 of the insertion section cover 22 from being contaminated, the cover supporting member 27 may be covered with a disposable cover. As will be explained later, the connecting portion 25 of the insertion section cover 22 is utilized to couple the insertion section cover with the operation section cover 23.

A height of the cover supporting member 27 has to be adjusted such that when the insertion section cover 22 is hung from the cover supporting member 27, the distal end of the disposable insertion section cover is not brought into contact with a floor. However, if a height of the cover supporting member 27 is made too high, the inserting operation becomes difficult, so that the cover supporting member could not be made so high. In such a case, the insertion section cover 22 has to be supported by an operator.

After the insertion section cover 22 has been hung from the cover supporting member 27, an end of an air supply tube 28 connected to the inflator 19 is coupled with a nipple portion 29 provided in the connecting portion 25 of the insertion section cover 22, and then the inflator 19 is driven to supply an air through the tube 28 into insertion section cover 22. In this manner, the insertion section cover 22 is inflated, so that the insertion section 11 of the endoscope 13 can be easily inserted into the insertion section cover 22. Then, the inflator 19 is de-energized and the tube 28 is decoupled from the nipple portion 29. This inflating operation is also performed upon removing the insertion section 11 from the insertion section cover 22. After the examination, the protection covers 22, 23 and 24 are discarded as medical dusts and the endoscope is cleaned and sterilized after all examinations for one day have been finished.

FIG. 2 shows the construction of the operation section 12 of the endoscope. To the operation section 12 are connected the insertion section 11 and universal cord 21. The operation section comprises a grip portion 31 and a main portion 32. The main portion 32 comprises angle knobs 33 for bending the distal end of the insertion section 11, air and water supply control switch 34, suction control switch 35 and function switches 36 for controlling the operation of a camera taking photographs of the object under inspection. In the present embodiment, the angle knobs 33 are detachably secured to the main portion 32 of the operation section 12. The angle knobs 33 may be of a disposable type and may be contained in a package in which the disposable protection cover is installed. Alternatively the angle knobs may be reused after sterilization. To the universal cord 21 is connected a connector 21a for connecting a light guide optical fiber bundle 39, conduit tubes and signal conductors to the external apparatus 14.

FIG. 3 is a perspective view illustrating the construction of the insertion section 11 of the endoscope. In the present embodiment, a lateral cross section of a distal end construction member 37 is semicircular and in a front surface 38 of the member 37 there are arranged outlets of a pair of illuminating optical systems, i.e. optical fiber bundles 39 and an observing optical system 40 provided between the illuminating optical systems.

FIG. 4 is a perspective view depicting the construction of a distal end of the insertion section cover 22 and FIG. 5 is a longitudinal cross sectional view showing the insertion section cover 22 into which the insertion section 11 of the endoscope is inserted. In a front surface of a distal end construction member 41 of the insertion section cover 22, there are provided a semicircular observation window 42 made of transparent material, a nozzle 43 for ejecting air and water toward the window 42, and an outlet opening 44 of a forceps channel 52. By ejecting the air and water from the nozzle 43, the outer surface of the observation window 42 can be cleaned.

To the distal end construction member 41 of the insertion section cover 22, is connected one end of an insertion section cover tube 45 which isolates a main portion of the insertion section 12 from the external. This cover tube 45 is made of a flexible material. In the present embodiment, the flexible cover tube 45 is formed as a multilayer construction and comprises a middle layer 45a made of photosensitive material such as silver halide and opaque inner and and outer layers 45b and 45c as shown in FIG. 6. The other end of the cover tube 45 is connected to the connecting portion 25 of the insertion section cover 22.

By constructing he flexible cover tube 45 in the manner explained above, it is possible to detect a pin hole formed therein in an easy and positive manner. That is to say, when a pin hole is formed in the inner layer 45b. light is made incident upon the middle layer 45a made of photosensitive material and a color of an exposed portion of the middle layer is changed. This change in the color of the middle layer 45a can be easily monitored and thus the pin hole can be detected easily. When the pin hole is detected, the relevant disposable protection cover is replaced by a new one. In this manner, a possible contamination through the pin hole can be prevented.

As illustrated in FIG. 5, within the distal end construction member 37 of the insertion section 11 which is faced with the observation window 42 of the distal end construction member 41 of the insertion section cover 22, there are arranged observing lens system 46 for forming an image of an object under inspection and a solid state image sensor 47 for picking-up the image of an object under inspection. The solid state image sensor 47 is electrically connected to the video processor 15 (FIG. 1) by means of signal conductors 48 extending through the insertion section 11 and universal cord 21.

Within the insertion section cover 22, there are formed endoscope insertion channel 49 into which the insertion section 11 is inserted, air supply conduit channel 50 communicated with the air and water ejecting nozzle 43, water supply conduit channel 51 also communicated with the nozzle 43, and forceps channel 52. These channels are arranged in parallel with each other. The forceps channel 52 is communicated with a forceps inlet opening 53 provided in the connecting portion 25 and is also communicated with the fluid control device 18 by means of a conduit tube provided within the universal cord 21. Therefore, the forceps channel 52 is sometimes called a suction channel. Further, the conduit channels 50, 51 and forceps channel are also called conduit tubes in the present specification.

In order to bend the distal end of the insertion section 11 by operating the angle knobs 33 such that an optical axis of the observing optical system 46 is moved up and down as well as right and left, there is provided a bending portion 54 adjacent to the distal end construction member 37 of the insertion section 11 of the endoscope. The bending portion 54 comprises a series of nodal rings 55 which are coupled with each other by means of journal pins 56 and a front end ring is connected to the distal end construction member 37 of the insertion section 11. A pair of wires 57, 58 are secured to the front end ring 55 at diametrically opposing points. These wires 57, 58 are extended within the insertion section 11 and are wound around a pair of pulleys provided in the operation section 12. In FIG. 5, only the wire 57 is shown, but the other wire 58 is illustrated in FIG. 10. A series of nodal rings 55 is covered with a flexible rubber tube 59 in a liquid tight manner. By operating the angle knobs 33, the pulleys may be rotated and thus the wires 57, 58 may be moved so as to direct the distal end of the insertion section 11 into a desired direction. This construction is well known in the art, so that its detailed explanation may be dispensed with. At a proximal end of the connecting portion 25 there are formed a ring shaped recess 25a for connecting the operation section cover 23 and a ring shaped recesses 25b for engaging the connecting portion with the supporting member 27 on the supporting stand 26.

As illustrated in FIG. 5, in the outer surface of the connecting portion 25, there are formed flange 25a and ring shaped recesses 25b and 25c. The operation section cover 23 comprises a first portion 23a made of semi-rigid material and a second portion 23b formed by a flexible tube. An end of the first portion 23a is secured to the flange 25a of the connecting portion 25 while one end of the second portion 23b is clamped between the flange 25a and the first portion 23a. The other end of the second portion 23b is secured to the ring shaped recess 25c by means of a rubber band 23c.

The ring shaped recess 25b serves to support the insertion section cover 22 onto the supporting member 27 as will be explained in detail.

FIG. 7 is a schematic view showing the general conception of the endoscope system according to the invention. According to the invention, the operation section cover of the disposable protection cover is constructed to be used commonly for various types of the endoscopes. As shown in FIG. 7, the operation section cover 23 can be used for different endoscopes 13A and 13B whose insertion sections are different from each other, so that it is necessary to prepare insertion section covers 22A and 22B. As depicted in FIG. 8, the insertion section 11A of the endoscope 13A has different length and diameter from the insertion section 11B of the endoscope 13B, so that the insertion section covers 22A and 22B have different length and diameter. However, the operation section 12A of the endoscope 13A is substantially same as the operation section 12B of the endoscope 13B, so that the operation section cover 23 can be commonly used for the endoscopes 13A and 13B. It should be noted that FIG. 8 shows only the embodiments of the endoscopes having different insertion sections and various embodiments may be conceived by those skilled in the art.

FIG. 9 shows a mechanism for detachable securing the angle knobs 33 to a shaft 61 provided in the operation section 12 of the endoscope. The operation section 12 is covered with the operation section cover 23. In this operation section cover 23, there is formed an aperture 62 through which the shaft 61 is extended from the cover 23. A diameter of the aperture 62 is much smaller than a diameter of the shaft 61, so that the contamination via this aperture can be reduced to a great extent. In the present embodiment, the distal end of the insertion section 11 of the endoscope may be bent right and left as well as up and down, and thus there are provided a right and left angle knob 33-1 and an up and down angle knob 33-2.

FIG. 10 is a cross sectional view illustrating the detailed construction of the detachably securing mechanism of the angle knobs 33-1 and 33-2 to the shaft 61, and FIG. 11 is a cross sectional view cut along a line 11—11 in FIG. 10. Within a housing of the operation section 12 there are arranged the pair of pulleys 64 and 64. The lower pulley 64 is integrally formed with a base portion of a first rotary shaft 66 in the form of a cylinder, and the wire 58 is wound around the pulley 64. The first rotary shaft 66 is rotatably supported by a supporting rod 68 which is secured to a base 67 provided in the housing 63. A front end portion of the first rotary shaft 63 is protruded from the housing 63 as well as from the operation section cover 23 and the first right and left angle knob 33-1 may be detachably secured to the thus protruded front end portion of the first rotary shaft by means of a nut 69. The second pulley 65 is formed integrally with a base portion of a second rotary shaft 70 which is rotatably provided around the first rotary shaft 66, so that the first and second rotary shafts 66 and 70 are arranged coaxially with each other. The wire 57 is wound around the second pulley 65. The second rotary shaft 70 is journalled by a bearing 71 secure to the housing 63. A front end portion of the second rotary shaft 70 is protruded from the housing 63 and operation section cover 23. In this case, the second rotary shaft 70 is extended below the lower surface of the first angle knob 33-1. As clearly shown in FIG. 11, the front end 72 of the second rotary shaft 70 is shaped to have a rectangular cross section. In a center of the second up and down angle knob 33-2 there is formed a rectangular opening 72 corresponding to the rectangular front end 72 of the second rotary shaft 70. In this manner the second angle knob 33-2 may be detachably secured to the front end 72 of the second rotary shaft 70 by inserting the rectangular front end into the rectangular opening 73. There are further provided sealing members 74, 75 and 76 between the first rotary shaft 66 and the supporting rod 68, between the first and second rotary shafts 66 and 70, and between the second rotary shaft 70 and the bearing 71, respectively. In this manner, in the present embodiment, the supporting rod 68 and first and second rotary shafts 66 and 70 constitute the shaft 61.

FIG. 12 illustrates the construction of an embodiment of the operation section 12 of the endoscope. In the present embodiment, the universals cord 21 is connected to the operation section 12 by means of a fitting 21b made of elastic material such as silicon rubber. The fitting 21b serves to prevent the universal cord from being bent at the fitting. On the operation section 12 in addition to the air supply switch 34, water supply switch 35 and operation switches 36, there is provided a suction switch 80. When the suction switch 80 is operated, the liquid is sucked from the forceps outlet opening 44 through the forceps channel 52. It should be noted that in this case, the forceps inlet opening 53 is closed.

FIG. 13 is a perspective view showing an embodiment of the operation section cover 23 according to the invention. According to the invention, the operation section cover is constructed such that it can be used commonly for various types of operation sections. In the present embodiment, the operation section cover 23 comprises main body and lid body 81 and 82 made of semi-rigid plastics. However, portions 83 of the main body 81 corresponding to the switches 34, 35, 36 and 80 are made of resilient material. In corresponding side walls of the main body and lid body 81 and 82, there are formed substantially semicircular projections 84 and 85, respectively which form an opening through which the universal cord 21 protruded from the operation cover 23 when the main body and lid body are coupled with each other. In outer walls of tips of the projections 84 and 85, there are formed recesses 86 and 87, respectively for connecting the universal cord cover 24 to the operation section cover 23.

As illustrated in FIG. 14, in the main body 81, there is formed an aperture 88 through which the shaft 61 is protruded from the operation section cover 23. Moreover, in outer surfaces of the main body 81 and lid body 82 there are formed non-slip ridges 89 and 90 at portions corresponding to the grip portion 31 of the operation section 12. In a side edge of the main body 81 there are formed a plurality of holes 91 and in a side edge of the lid body 82 there are formed corresponding projections 92. Therefore, by inserting the projections 92 into corresponding holes 91, the main body 81 and lid body 82 can be firmly coupled with each other as shown in FIG. 15.

As shown in FIG. 5, the operation section cover 23 is formed by the first portion 23a and tube-like second portion 23b, so that strictly speaking only the construction of the first portion 23a is shown in FIG. 13. FIG. 15 shows the operation section cover 23 by means of which the operation section 12 of the endoscope is enclosed. One end of the second portion 23b is clamped between the connecting portion 25 and the first portion 23a as illustrated in FIG. 5. FIG. 16 is a bottom view of the main body 81 and lid body 82. In the bottom of the main body 81 there is formed a recess 93 into which the insertion section 11 of the endoscope is insertable, and in the lid body 82 there is formed a projection 94. When the main body 81 and lid body 82 are coupled with each other, the projection 94 is inserted into the recess 93 such that a circular space is formed therebetween.

A diameter of this circular space is determined to be smaller than that of the flange 25a of the connecting portion 25 shown in FIG. 5.

Now the construction of the universal cord cover 24 will be explained. As shown in FIG. 17A, the universal cord cover 24 is formed by a flexible sheet which includes a binding member 24a at its one end. The universal cord 21 including the light guide and signal conductors and conduit tubes 101, 102 and 103 communicated with the air supply conduit channel 50, water supply conduit channel 51 and suction conduit channel (forceps channel) 52 are arranged side by side in parallel with each other and are surrounded by the universal cord cover 24 as shown by an arrow in FIG. 17A. A proximal end of the assembly is bound by a band 104 and then is fixed by an adhesive tape 105 as illustrated in FIG. 17B. A distal end of the universal cord cover 24 is wound around the projections 84, 85 of the operation section cover 23 and is bound by the binding member 24a into the recesses 86, 87 as shown in FIG. 18.

FIG. 19 is a perspective view depicting the disposable protection cover installed in a package. A package 110 has formed therein a plurality of guides 111 and the disposable protection cover is installed along these guides 111. In this manner, the whole size of the package 110 can be made smaller, so that a necessary space for stocking the packages can be made also small. Further after the disposable protection cover has been set in the package 110, the whole body is sterilized. In this case, the disposable protection cover can be sufficiently brought into contact with a sterilizing gas, so that the sterilization can be carried out effectively.

FIG. 20 is a perspective view showing the holding device 26 for holding insertion section cover 22 of the disposable protection cover. The supporting device 26 comprises a stand 115, supporting member 116 (corresponding to the supporting member 27 in FIG. 1) and level adjusting ring 117 having a screw 118. By operating the screw 118, a height of the supporting member 116 can be adjusted at will such that the distal end of the insertion section cover 22 is not brought into contact with the floor. Upon hanging the insertion section cover 22 from the supporting member 116, the supporting member 116 is inserted into the ring shaped recess 25b formed in the outer surface of the connecting portion 25 as illustrated in FIG. 5.

After the examination, the insertion section of the endoscope is removed from the insertion section cover and then the used insertion section cover may be discarded. However, in this case, the liquid is usually remained in and on the insertion section cover, so that the liquid might dropped off the insertion section cover to cause the contamination. In order to avoid such a drawback, it is desired to wash the used insertion section cover with water. However, this washing is very cumbersome and requires a rather long time.

FIG. 21 is a perspective view showing an apparatus for washing the used insertion section cover. The washing apparatus comprises a hanging device 121 including a stand 122 secured to a base 123 and a supporting member 124 secured to the stand 123. The operation section cover 23 is supported by the supporting member 124 so that the insertion section cover 22 is hung from the supporting member. On the base 123 there is provided a switch 125 and a vessel 126 is placed on the base at the position of the switch 125. When the vessel 126 is in place, the switch 125 is turned on. Although, 25 illustrated in FIG. 24, the switch 125 may be provided on the supporting member 124 at such a position that when the operation section cover is hung on the supporting member 124, the switch 125 is automatically turned ON.

FIG. 22 shows a diagram showing the construction of the washing apparatus. In FIG. 22, the switch 126 is connected to a controller 127 for controlling open and close of valves 128, 129 and 130 in accordance with timings shown in FIG. 23. An air pump 131 is connected to the valve 128 as well as to a water tank 132 which is connected to the valve 129. There is further provided a suction pump 133 which is connected to the valve 130. The valve 128 is connected to the air supply conduit tube 50 by means of a quick disconnect coupling 134, the valve 129 is connected to the water supply conduit tube 51 via a quick disconnect coupling 135, and the valve 130 is coupled with the suction conduit tube 52. It should be noted that the valves 128 to 130, pumps 131 and 133 and quick disconnect couplings 134, 135 are all provided in the fluid control device 18 of the external apparatus 14 shown in FIG. 1, so that the washing apparatus can be constructed simply and does not increase the cost of the endoscope system.

Now the operation for covering the endoscope with the disposable protection cover will be explained with reference to FIG. 20. This operation is carried out by two operators, one operator A for a non-contaminated area and the other operator B for a contaminated area. The operator A puts on sterilized clean gloves and takes the sterilized disposable protection cover from the package 110 shown in FIG. 19. At first, the operator A inserts the proximal end of the connecting portion 25 of the insertion section cover 22 into the second tube-like operation section cover 23b and then the second cover 23b is connected to the ring shaped recess 25c of the connecting portion 25 by means of the rubber band 23c. Then, the operator A inserts the ring shaped recess 25b of the connecting portion 25 into the supporting member 116 of the insertion section cover supporting device 26. In this manner, the insertion section cover 22 is hung from the supporting member 116 as shown in FIG. 20.

Next the operator B connects the inflate tube 28 to the nipple portion 29 provided in the connecting portion 25 shown in FIG. 1 and operates the inflator 19 to inflate the insertion section inserting channel 49. Then the operator B inserts the insertion section 11 of the endoscope into the insertion section inserting channel 49 until the distal end of the insertion section 11 is firmly inserted into the corresponding hole formed in the distal end construction member 41 of the insertion section cover 22 and the distal end of the operation section 12 is coupled with the connecting portion 25. Further the operator B holds the tubes 101 to 103 extending from the connecting portion 25 along the universal cord 21. Then, the operator A inserts the shaft 61 extending from the operation section 12 into the aperture 88 (FIG. 14) formed in the main body 81 of the first operation section cover 23a, and inserts the conduit tubes 101 to 103 into the main body 81. After that, the operator A couples the lid body 82 with the main body 81. During this operation, the second operation section cover 23b is clamped between the connecting portion 25 and the first operation section cover 23a. Then, the angle knobs 33 are secured to the shaft 61. Next the operator A raps the universal cord 21 as well as the conduit tubes 101 to 103 with the universal cord cover 24 and fixes then by means of the adhesive tape 105 as shown in FIG. 17B. The operator A sets one end of the universal cord cover 24 onto the projections 84, 85 (FIG. 13) and fixes the cover to the projections by means of the binding member 24a as illustrated in FIG. 18. Further the operator A sets the other end of the universal cord cover 24 onto the connector 21a and fixes it by means of an adhesive tape. Finally the operator B connects the connector 21a to the light source device 17, connects the connector 21a to the video processor 15 by means of a cable 15a (FIG. 1), connects the tubes 101 to 103 to the fluid control device 18, and disconnects the inflating tube 28 from the nipple portion 29. In this manner, the insertion section and operation section of the endoscope can be covered with the sterilized clean disposable protection cover.

Next the operation for removing the endoscope from the disposable protection cover after the examination will be explained. At first the vessel 126 containing the water is place on the base 123 of the protection cover discarding apparatus 121 and the the endoscope with the used cover is hung from the supporting member 124. Then, the switch 125 is made ON and the valves 128 to 130 is driven as represented by a table shown in FIG. 23. That is to say, the valves 128 to 130 are successively operated to supply the air through the air supply tube 50, then the water is supplied through the water supply tube 51 and finally the water is sucked through the suction tube 52. In this manner, the used cover is washed effectively. In the present embodiment, the washing operation is automatically started by placing the vessel 126 on the switch 125 so that the operation efficiency is improved.

Then a dust box is prepared and the tubes 101 to 103 are removed from the fluid control device 18 and the cable 15a is disconnected from the connector 21a. Then, the universal cord cover 24, angle knobs 33 and first operation section cover 23a are removed and are discarded in the dust box. Further the second operation section cover 23b and rubber band 23c are discarded in the dust box.

Next the endoscope with the insertion section cover 22 is hung on the supporting member 116 of the insertion section cover supporting apparatus shown in FIG. 20. Then, the inflating tube 28 is connected to the nipple portion 29 provided in the connecting portion 25 of the insertion section cover 22 and the insertion section inserting channel 49 within the insertion section cover 22 is inflated. Then, the insertion section 11 of the endoscope is removed from the insertion section cover 22. After that the insertion section cover 22 is discharged in the dust box. It should be noted that the endoscope is used together with a new disposable protection cover without cleaning the endoscope. After all examinations for a day have been finished, the endoscope is cleaned and sterilized.

Figure 25:
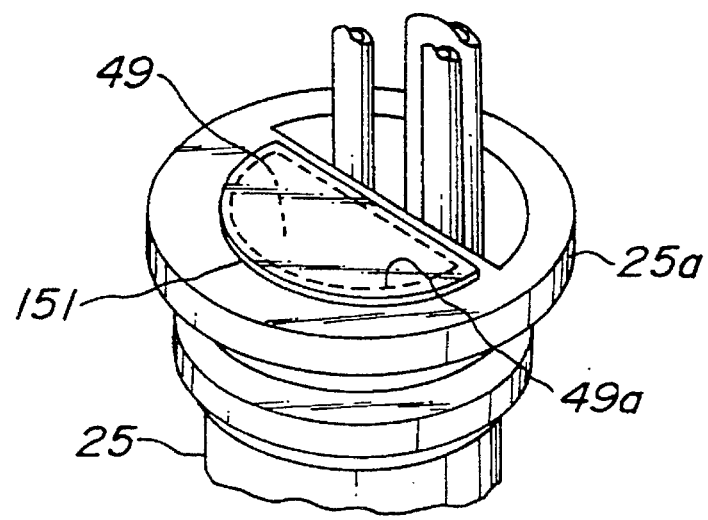
FIG. 25 is a perspective view showing an embodiment of the lid-like member for closing the insertion section inserting opening according to the invention.
Figure 26:
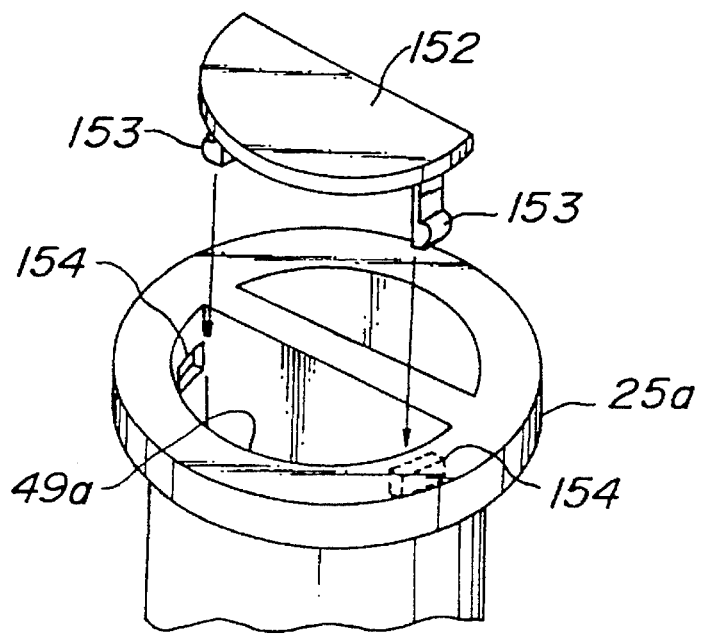
FIG. 26 is a perspective view illustrating another embodiment of the lid-like member.

As stated above, when the insertion section 11 of the endoscope is inserted into the insertion section cover 22, the insertion section inserting channel 49 is inflated by supplying the air from the inflator 19 and the insertion section is inserted from the opening of the channel 49. In order to avoid dust (or other contamination) from being introduced inside the insertion section cover 22 through the opening of the insertion section inserting channel, it is desired to close said opening of the channel 49 by means of a lid-like member. FIG. 25 is a perspective view showing an embodiment of such a lid-like member. In this embodiment, a protection film 151 made of plastics and having an adhesive on its rear surface is applied onto the end face of the connecting portion 25 at a portion where an opening 49 of the insertion section inserting channel 49 appears. Upon inserting the insertion section of the endoscope into the channel 49, the protection film 151 is pealed off the connecting portion 25. Alternatively the insertion section 11 may be pierced into the protection film 151 when the film is made of a thin film. FIG. 26 illustrates another embodiment of the lid-like member, in which a cap 152 having projections 153 is inserted into the opening 49a of the insertion section inserting channel 49 such that the projections 153 is snapped into recesses 154 formed in the inner wall of the channel.

By providing the above mentioned lid-like member 151, 152, the intrusion of dusts into the insertion section inserting channel 49 can be effectively prevented. Further, the insertion section inserting channel 49 can be inflated effectively by the lid-like member, a pin hole can be easily detected.

FIGS. 27A and 27B show another embodiment of the universal cord cover of the disposable protection cover according to the invention. Portions similar to those shown in FIGS. 17A and 17B are denoted by the same reference numerals used in FIGS. 17A and 17B. In the present embodiment, a plurality of bands 160 are provided on an inner surface of the universal cord cover 24. That is to say, both ends of the bands 160 are secured to the universal cord cover 24 by adhesive agent or fusing. The bands 106 may be made of the same material as the universal cord cover 24. Before rapping the tubes 101 to 103 and the universal cord 21 by the universal cord cover 24, the tubes are inserted in spaces formed between the bands 160 and the universal cord cover 24, and thus the tubes can be fixed easily and positively.

FIGS. 28 to 30 show several embodiments of the tube holding member provided in the universal cord cover 24. In the embodiment illustrated in FIG. 28, a tube holding member 161 is made of resilient plastics and a bottom of a base portion 161a is secured to the inner wall of the universal cord cover 24 by adhesive agent. The tube is resiliently inserted into a fixing portion 161b. In the embodiment shown in FIG. 29, a tube holding member 162 is formed by double-side adhesive tape and one surface of the tape is secured onto the universal cord cover 24. In the embodiment depicted in FIG. 30, a tube holding member 163 is formed by an adhesive tape and one end of the tape is secured to the universal cord cover 24. In the embodiments shown in FIGS. 28 to 30, the tube holding members 161 to 163 are secured to the universal cord cover 24, but these tube holding members may be secured onto the universal cord.

Figure 31:
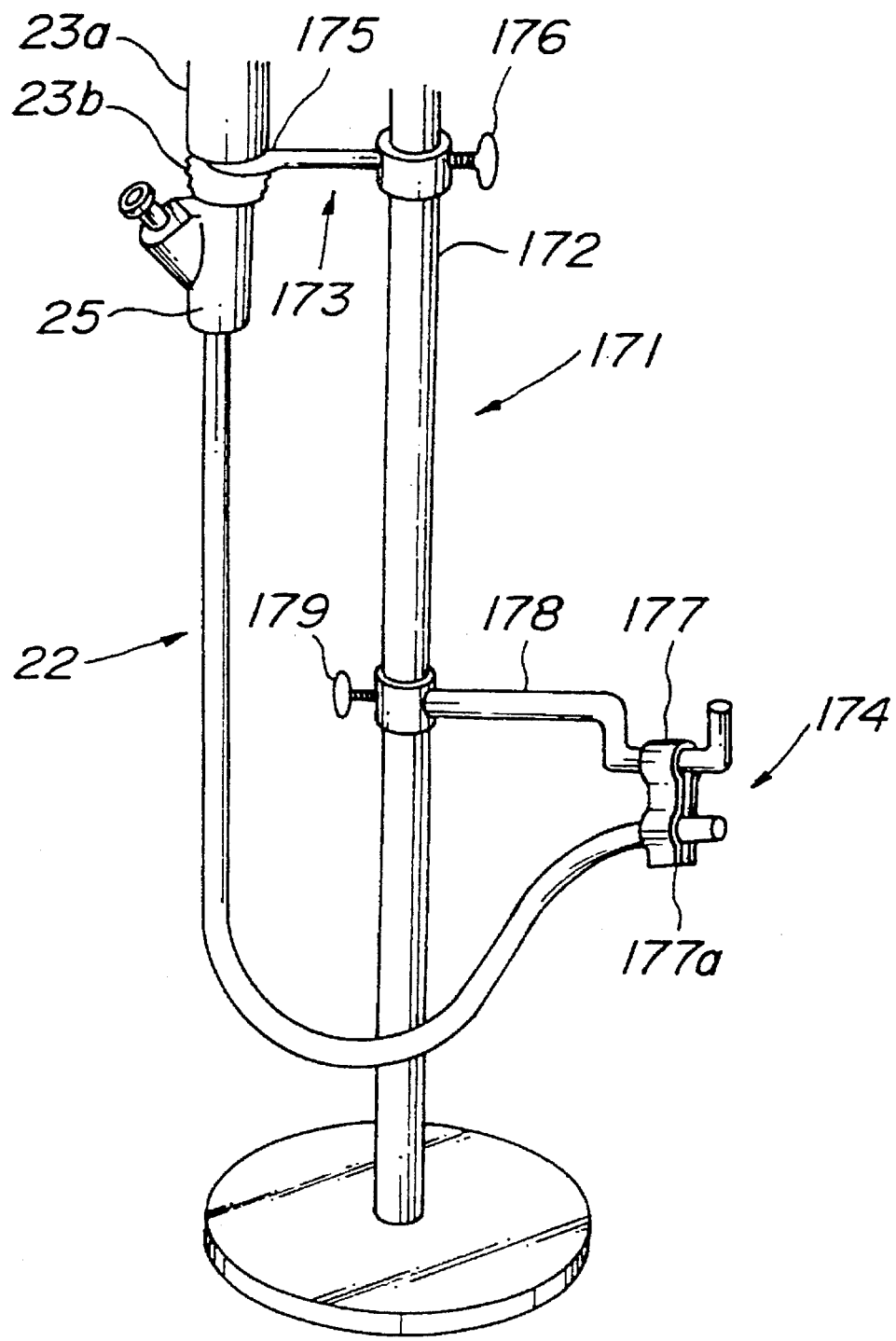
FIG. 31 is a perspective view showing another embodiment of the supporting apparatus according to the invention.

FIG. 31 is a perspective view showing an embodiment of the apparatus for supporting the assembly of the endoscope and disposable protection cover according to the invention. According to the invention, the supporting apparatus is constructed such that it can support the assembly of the endoscope and disposable protection cover at at least two points. A supporting apparatus 171 comprises stand 172, proximal end supporting unit 173 and distal end supporting unit 174. The proximal end supporting unit 173 includes a supporting member 175 which is engaged with the ring shaped recess 25b formed in the outer surface of the connecting portion 25 of the insertion section cover 22 as shown in FIG. 5. A height of the supporting member 175 can be adjusted by means of an adjusting screw 176 in accordance with a length of the insertion section cover 22. The distal end supporting unit 174 comprises a holding member 177 for holding the distal end of the insertion section cover 22, a hunger 178 for supporting the holding member 177 and an adjusting screw 179 for adjusting a height of the hunger 178 on the stand 172. The holding member 177 is made of resilient material and the distal end of the insertion section cover 22 can be easily clamped by the holding member by widening a space formed between tip portions 177a thereof. It should be noted that the holding member 177 is discarded together with the used disposal protection cover.

The operation for inserting and removing the endoscope into and from the disposable protection cover after the examination is substantial same as that explained above with reference to FIGS. 20 and 21. However, in the present embodiment, the distal end of the insertion section cover 22 is supported by the distal end supporting unit 174. Therefore, in the present embodiment, the long insertion section cover 22 can be treated without being brought into contact with the floor.

Figure 32:
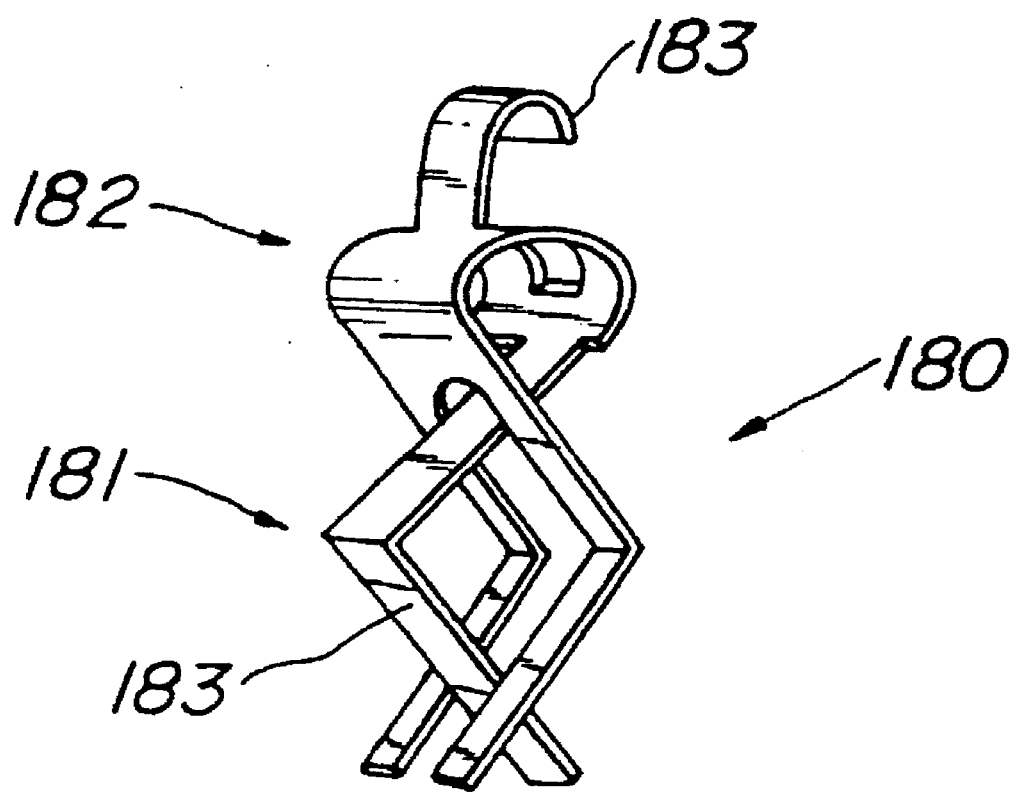
FIG. 32 is a perspective view depicting another embodiment of the tube holding member according to the invention.

FIG. 32 is a perspective view showing another embodiment of the holding member of the distal end supporting unit 174. In the present embodiment, a holding member 180 is made of a resilient material such as a leaf spring and has an clamping portion 181, a bending portion 182 and a hook portion 183. A space formed by the clamping portion 181 under the free condition is set to be smaller than a cross sectional area of the distal end of the insertion section cover 22. When the distal end of the insertion section cover is held, the bending portion 182 is pushed inwardly against the resilient force of the bending portion to make said space larger. Then, the distal end of the insertion section cover is inserted into the widened space, and after that the bending portion 182 is made free. In this manner, the distal end of the insertion section cover can be held firmly by the holding member 180. It should be noted that the holding member 180 is also of disposable type.

Figure 33:
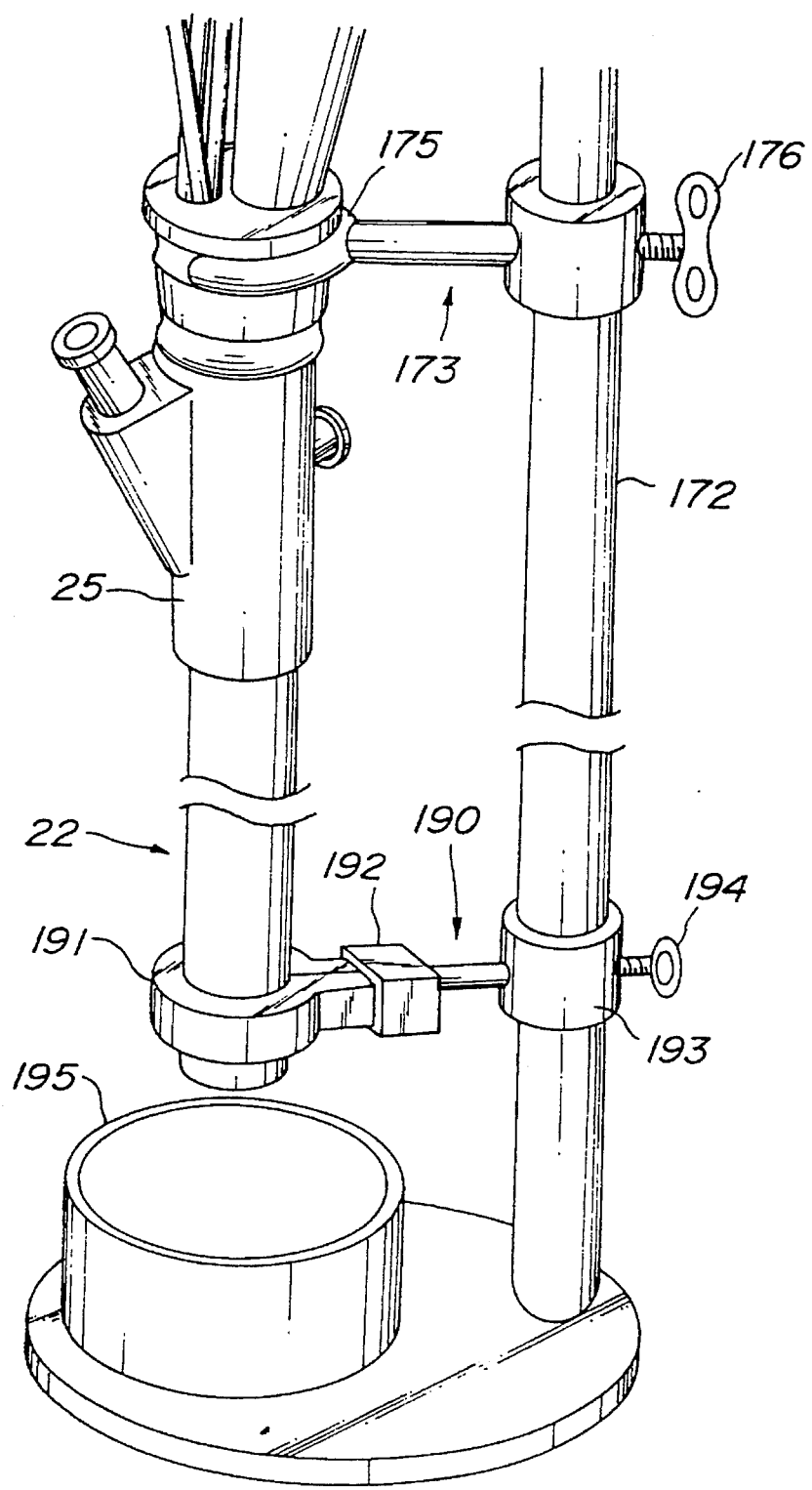
FIG. 33 is a perspective view showing another embodiment of the supporting apparatus according to the invention.

FIG. 33 is a perspective view illustrating another embodiment of the insertion section supporting apparatus according to the invention. In the present embodiment, portions similar to those shown in FIG. 31 are denoted by the same reference numerals used in FIG. 31. The construction of the proximal end supporting unit 173 is similar to that of the previous embodiment shown in FIG. 31. A distal end supporting unit 190 comprises clamping member 191, holder 192 into which arm-like portion of the clamping member 191 is detachably inserted, a level adjusting ring 193 with which the holder 192 is coupled by means of a rod and an adjusting screw 194. In the present embodiment, the proximal end supporting unit 173 and distal end supporting unit 190 are arranged such that the insertion section cover 22 is hung down straight. Below the distal end of the thus hung insertion section cover 22 there is arranged a dust box 195 into which the used disposable protection cover is discarded.

Figure 34:
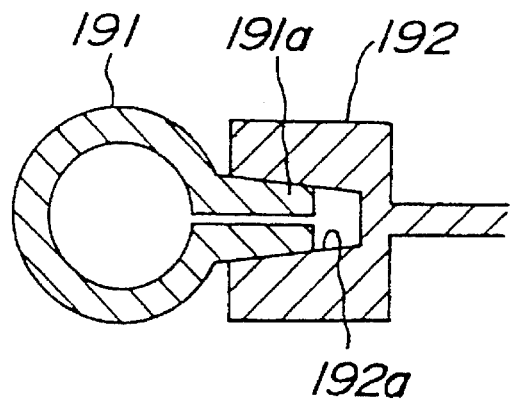
FIG. 34 is a cross sectional view of the distal end supporting unit shown in FIG. 33.

FIG. 34 is a cross sectional view showing the construction of the clamping member 191 and holder 192. The clamping member 191 is made of semi-rigid material and has the projections 191a which are formed such that a distance between opposing side surfaces is decreased toward tips of the projections, and the holder 192 has a hole 192a formed therein, said hole being tapered corresponding to the tapered projections 191a.

Figure 35:
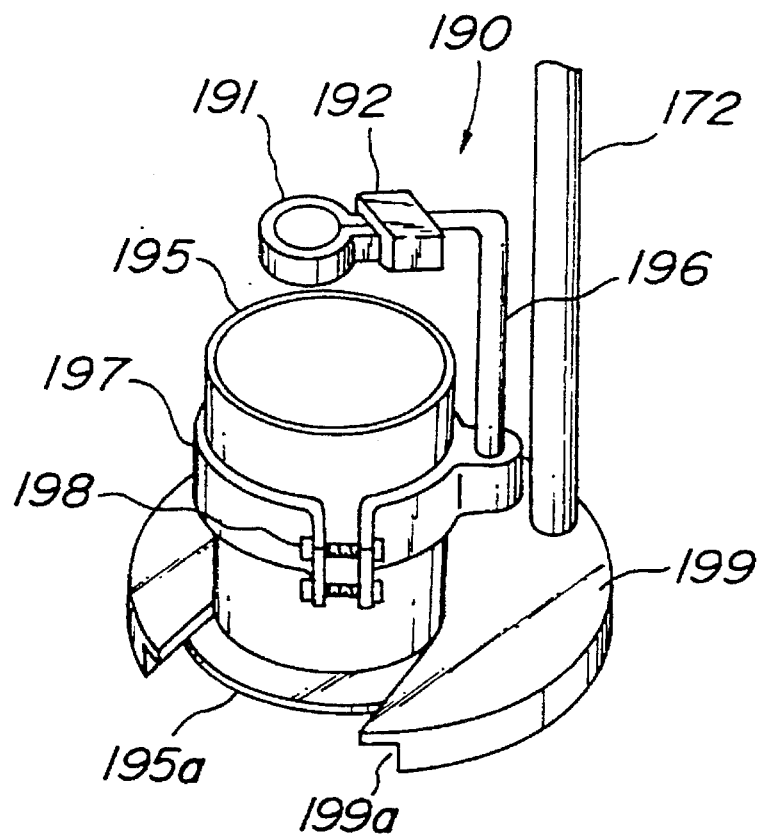
FIG. 35 is a perspective view showing still another embodiment of the supporting apparatus according to the invention.

FIG. 35 is a perspective view showing another embodiment of the supporting apparatus according to the invention. In the present embodiment, portions similar to those of the embodiment illustrated in FIG. 33 are denoted by the same reference numerals used in FIG. 33. In the this embodiment, the distal end supporting unit 190 is secured to the dust box 195 by means of a rod 196, a level adjusting ring 179 and adjusting screws 198. The dust box 195 has a relatively large height and the ring 197 may be fixed on the dust box at any desired position, so that a level of the clamping member 191 can be adjusted in accordance with a length of the insertion section cover 22. The stand 172 is secured to a base 199 having a recess 199a into which a flange 195a formed at the bottom of the dust box 195 is detachably inserted. In the present embodiment, the distal end supporting unit 190 is coupled with the dust box 195, and thus the dust box is always existent below the distal end of the insertion section cover. Further, the dust box 195 is supported by the base 199, so that the dust box is hardly knocked over.

What is claimed is:

1. An apparatus for washing a protection cover for use in an endoscope system including an endoscope having an insertion section insertable into a cavity under inspection and an operation section to which a proximal end of the insertion section is connected and a protection cover having an insertion section cover for covering said insertion section of the endoscope and an operation section cover for covering said operation section of the endoscope, said insertion section cover having an air supply conduit channel, a water supply conduit channel and a suction channel formed therein, said washing apparatus comprising:

means for supporting said protection cover in such a posture that the distal end of the insertion section cover is directed toward the ground;

means for containing a liquid into which said distal end of the insertion section cover is immersed; and means for automatically starting a washing operation, said washing operation being performed by supplying air through said air supply conduit channel, thereafter supplying water through said water supply conduit channel and thereafter sucking liquid through said suction channel.

2. A washing apparatus according to claim 1, wherein said means for automatically starting the washing operation comprises a switch for detecting a condition that said liquid containing means is operatively associated with the washing apparatus.

3. A washing apparatus for washing a protection cover for use in an endoscope system including an endoscope having an insertion section insertable into a cavity under inspection and an operation section to which a proximal end of the insertion section is connected and a protection cover having an insertion section cover for covering said insertion section of the endoscope and an operation section cover for covering said operation section of the endoscope, said insertion section cover having an air supply conduit channel, a water supply conduit channel and a suction channel formed therein, said washing apparatus comprising:

means for supporting said protection cover in such a posture that the distal end of the insertion section cover is directed toward the ground;

means for containing a liquid into which said distal end of the insertion section cover is immersed; and means for automatically starting a washing operation, said washing operation being performed by supplying air through said air supply conduit channel, thereafter supplying water through said water supply conduit channel and thereafter sucking liquid through said suction channel, said means for automatically starting the washing operation comprising a switch provided in said supporting means for detecting a condition that the protection cover is operatively associated with said supporting means.

* * * * *